United States Patent [19]
Heiman et al.

[11] Patent Number: 5,424,117
[45] Date of Patent: Jun. 13, 1995

[54] FABRICS FOR SURGICAL GOWNS AND THE LIKE AND METHOD OF MAKING SAME AND TEXTILE PRODUCTS MADE THEREFROM

[75] Inventors: Gary L. Heiman, Cincinnati, Ohio; John M. Smith; C. Dean Goad, both of Greensboro, N.C.

[73] Assignees: Standard Textile Co. Inc., Cincinnati, Ohio; Precision Fabrics Group, Inc., Greensboro, N.C.

[21] Appl. No.: 827,759

[22] Filed: Jan. 29, 1992

Related U.S. Application Data

[63] Continuation-in-part of Ser. No. 546,354, Jun. 29, 1990, abandoned.

[51] Int. Cl.$^6$ .................. A61B 19/08; A61F 13/00; B32B 33/00; D03D 15/00; D06P 5/02; D06P 7/00
[52] U.S. Cl. .................................... 428/229; 8/491; 8/494; 8/495; 8/138; 8/157; 28/167; 28/168; 28/169; 38/52; 128/846; 128/849; 139/426 R
[58] Field of Search .............. 8/491, 494, 495, 138, 8/157; 28/167, 168, 169; 38/52; 128/846, 849; 139/426 R; 428/229

[56] References Cited
U.S. PATENT DOCUMENTS
4,822,667 4/1989 Goad et al. .................. 428/265

Primary Examiner—James C. Cannon
Attorney, Agent, or Firm—Kinney & Schenk

[57] ABSTRACT

Three reuasable surgical/medical fabrics provide improved barrier properties, as reflected by their Suter ratings, and also posses a "hand" similar to a "cotton hand". The Suter ratings are degraded in the order of 10%–20% after 100 sterile reprocessing cycles. The fabrics are reliable free of "voids", permitting their use as a single layer barrier panel. The fabrics are woven, respectively, with false twist 100/100 warp yarns and air texturized core and effect 2/60/100 fill yarns; flat trilobal 100/50 warp yarns and air texturized core and effect 2/60/100 fill yarns; and false twist 2/50/34 warp yarns and false twist 150/200 fill yarns. The fabrics are characterized by a minimum porosity of at least $10 \times 10^6$ pores/square centimeter and maximum average. and mean pore sizes. The fabrics have a thickness of at least 0.005 inch, a weight of at least 3.5 ounces per square yard and a filament density of at least $2.0 \times 10^6$ filaments per square inch. Filament density is obtained by increasing the number of picks in the greige construction to at least about 160 in the finished fabric. In two of the fabrics, the bulk of the greige construction is increased by "mechanically" working the fabric in a "jet dyeing machine".

75 Claims, 8 Drawing Sheets

EXAMPLE 1

EXAMPLES 2 & 4

EXAMPLE 3

FABRICS FOR SURGICAL GOWNS AND THE LIKE AND METHOD OF MAKING SAME AND TEXTILE PRODUCTS MADE THEREFROM

This application is a continuation-in-part of application Ser. No. 546,354, filed Jun. 29, 1990, now abandoned.

The present invention relates to improvements in fabrics employed in the fabrication of surgical gowns, and other textile products employed in surgical or medical procedures, as well as in other uses having similar functional requirements. The invention also relates to improvements in methods for making such fabrics.

While not necessarily so limited, the present invention is motivated by the specific requirements for fabrics employed in the fabrication of gowns worn by surgeons and other personnel in an operating room during the performance of a surgical procedure. In brief, such surgical gowns cover a person's body, from the shoulders to below the knees to provide protection, for the wearer of the gown, from liquids, such as blood, and other body fluids, as well as liquids, such as saline solutions, employed in a surgical procedure. It is undesirable for such fluids to penetrate, or strike through the gown fabric during the performance of surgical procedures involving an expectable amount of fluids impinging on the gown.

The gown, and more specifically the gown fabric, serves to provide a barrier function. A second, highly desirable characteristic, if not a requirement, for a reusable gown fabric is that it be "breathable", i.e., gas permeable. The latter characteristic enhances the comfort of the wearer during a lengthy surgical procedure by permitting the escape of perspiration moisture vapor. Additionally gas permeability facilitates steam penetration during the sterilization portion of a sterile reprocessing cycle.

This leads to the fact that surgical gowns may be broadly categorized as disposable or reusable. Disposable gowns, as the name implies, are intended for a one time use and then discarded. Reusable gowns, in distinction, are intended for multiple uses, which requires that they must be laundered (i.e., washed and dried) and sterilized after each use, herein referenced as sterile reprocessing.

Disposable gowns are convenient to use and have a relatively low acquisition cost. The disadvantages of disposable gown fabrics are that they are fabricated of non-woven fabrics which are relatively stiff. This is to say that disposable surgical gown fabrics have a feel or "hand" which many find undesirable and distracting when attempting to perform or assist in the performance of a surgical procedure. Additionally disposable gown fabrics are generally inferior in providing sufficient breathability for wearer comfort.

Reusable gowns are fabricated of a textile fabric, i.e., a yarn construction. Early surgical gowns were fabricated of tightly woven cotton yarns. Such gowns were comfortable when worn, but provided only minimal barrier protection for the wearer.

In order to provide some measure of barrier properties, surgical gowns were fabricated of spun yarns employing polyester staple in whole or in part. Such spun yarn fabrics, when provided with a hydrophobic finish at least partially met the barrier requirements for surgical gowns, and further had a "hand" quite similar to 100% cotton fabrics. However these spun fabrics found limited acceptance due to difficulties in maintaining the requisite barrier properties after any substantial number of sterile reprocessing cycles.

The problem of providing adequate barrier protection in reusable surgical gowns was overcome by the use of polyester, surgical gown fabrics, which were capable of maintaining their barrier properties to an acceptable degree, after 75 or more sterile reprocessing cycles. Such fabrics, as taught in U.S. Pat. No. 4,822,667, have found widespread commercial acceptance.

Reusable gowns have a higher acquisition cost, but a lower per use cost is achieved if the gown can be reused a sufficient number of times.

The number of times a surgical gown can be reused is a function of the extent to which its fabric can maintain the requisite barrier properties at acceptable levels after repeated laundering/sterilization. The laundering/sterilization cycle, sterile reprocessing cycle for surgical products (detailed below), is rigorous. The sterile reprocessing requirement makes most barrier fabrics, suitable for other purposes, unacceptable as a surgical gown fabric.

Another pertinent factor is that gown fabrics are "qualified" for a given number of times that they can be reused. This is to say that, based on empirical data, a fabric of a given construction is presumed safe for reuse if, when originally manufactured, the fabric has certain minimum barrier properties. Gowns fabricated of such "qualified" fabrics are used without further testing for a given number of times and then discarded. Currently, the maximum number of reuses is 75, for fabrics of conventional construction. This limitation is, additionally, a function of the methods employed in constructing such fabrics.

Fabrics constructed in accordance with the referenced U.S. Pat. No. 4,822,667 ('667 fabric(s)) have been "qualified" for use in reusable surgical gowns and, as indicated, have found significant commercial acceptance, being competitive, if not more economical than disposable gowns, on a per use basis.

Nonetheless, the '677 fabrics have certain shortcomings. For example, being a polyester fabric, the '677 fabrics have a "hand" which is perceptively dissimilar from the "hand" of a cotton fabric. Albeit that the "hand" of the '667 fabrics is an improvement over disposable gown fabrics, nonetheless it does not sufficiently approximate the "hand" of a cotton fabric to the extent desired by many surgeons and others who utilized surgical gowns. Further, while barrier properties can be increased beyond what is taught in the U.S. Pat. No. 4,822,667 patent, such improvements are achieved at the expense of a degradation in the "hand" characteristics.

Another shortcoming of the '677 fabric and similar prior art fabrics is that they tend to have random breakdowns in the integrity of the barrier function to the end that strikethroughs occur, during use, notwithstanding that the Suter rating of the fabric is at our acceptable level.

Such random breakdowns in the integrity of the barrier function can be the result of vagaries in the weaving process. That is, for example, small imperfections in the yarns can result in a "void" in the woven fabric, which in turn, can become the site of a strikethrough, when the fabric is incorporated in a surgical gown.

Random breakdowns in the integrity of the barrier function can also result from abuse of the fabric in use or in sterile reprocessing. Frequently, this type of breakdown involves the breaking of a yarn and a resultant "void", sometimes referred to as a "pin hole".

There is no economically feasible method of inspecting manufactured, surgical gown fabrics to assure that they are free of voids. Likewise there is no economically feasible method of inspecting surgical gowns, before each use, to assure that they are free of voids, which could potentially be the site of a strikethrough.

Strikethroughs resulting from such random breakdowns in the barrier function are relatively infrequent. Nonetheless, in order to provide an acceptable level of assurance that they will not occur, it has become an accepted practice to employ two layers of fabric in forming a barrier panel. A two layer barrier panel does not necessarily provide an absolute assurance against strikethroughs, but does give an acceptable level of assurance in that the incidence of strikethroughs in reduced to the order of one tenth of one percent of the number of times gowns are worn in the performance of a surgical procedure.

An ancillary drawback of prior art fabrics, such as the '677 fabric, is that their use as a doubled layer in a gown construction increases the cost of the gown, both in terms of amount of fabric used and the added costs of fabricating a two layer barrier panel.

A specific object of the present invention is to provide improvements in fabrics as taught in the aforesaid U.S. Pat No. 4,822,667.

To more fully appreciate the ends herein sought, pertinent characteristics of reusable surgical gown fabrics will now be discussed.

In order to assure that the barrier function is provided, the following objective measurements are made:

Water Resistance: Hydrostatic Pressure Test, (Suter)
Water Repellency: Spray Test
Oil Repellency: Hydrocarbon Resistance Test
Alcohol Repellency
Water Resistance: Impact Penetration Of these parameters for measuring the barrier capabilities of a fabric, the hydrostatic pressure test is the most critical. Generally speaking, if this characteristic meets a desired level, then the remaining, barrier characteristics will be at acceptable levels. The hydrostatic pressure test is commonly known as a Suter test and measures the resistance of a fabric to water penetration in terms of inch of hydrostatic head. More specifically the Suter rating is the hydrostatic head required for three drops of water to penetrate a fabric. For sake of brevity this measurement is referenced herein as a Suter rating, with measurement simply giving the number of centimeters, as a Suter rating of 80.

In describing various aspects of the present invention certain terms will be employed. These terms will now be defined for such purpose and for brevity in later discussion.

The yarns employed in the construction of the '667 fabrics, as well as the fabrics of the present invention, are commercially available. All yarns comprise continuous, multiple polyester filaments. The fact that the yarns comprise continuous, polyester filaments is to be inferred, where not specifically recited in connection with a given yarn.

A yarn is designated by its denier (weight in grams of a length of 9000 meters) and by the number of its filaments. A yarn, by convention, is designated in the following fashion—100/50 to indicated a yarn linear density of 100 denier comprised of 50 filaments (each of which would be of equal weight and, unless otherwise noted, of generally circular cross section).

A yarn may also comprise one or more "ends". In this connection an "end" is a bundle of filaments. Two or more "ends" can be combined in the forming of a single yarn. In some designations the number of ends is also designated. Thus a 1/150/75 yarn would be a single end of yarn having a denier of 150 and 75 filaments. A 2/60/100 yarn would be a yarn comprised of two "ends", with each end having a denier of 60 and 100 filaments, this double ended yarn thus has a nominal denier of 120 and a total of 200 filaments.

The filaments of a yarn are generally extruded as a straight length and then provided with a minimal twist to prevent separation of the filaments and maintain them as an integral yarn structure of generally circular cross section. This is known as a "flat" yarn.

There is a class of yarns known as "textured" yarns (also "texturized" yarns). In such yarns, the filaments are distorted from their generally rectilinear condition to increase the bulk of the yarn and also to provide an ability for a fabric woven therefrom to stretch. A textured yarn may be "set" by heat relaxation to minimize its stretch characteristic, while maintaining its increased bulk, i.e., higher bulked denier. The textured yarns, for sake of brevity, are not identified as being "set", but it is to be understood that they are "set".

There are several types of textured yarns capable of being produced by various methods. Different types of textured yarns have different characteristics, some being more expensive than others. The textured yarns employed in the present fabric constructions, or referenced herein, are:

False twist yarn is twisted in one direction, set, then twisted in the opposite direction and set. The twisting, setting, opposite twisting are repeated throughout the length of the yarn.

Core and effect yarn (also known as "core bulked" yarns) is a multiple ended yarn, usually comprising two ends in which one end is essentially straight. The filaments of other end are distorted around the core end and sometimes through the core end.

Air texturized core and effect yarn—is a core and effect yarn in which distortion of the filaments is done by air jet means. An air texturized core and effect yarn has unique properties which distinguish it from other textured yarns. These unique properties have been found effective in attaining the ends herein sought.

The above is not intended as an exhaustive definition of synthetic yarns, such being deemed unnecessary in view of the fact that all yarns herein are available from yarn producers. In other words, the present invention goes to improvements in fabric constructions and not to improvements in the yarns employed in such constructions. In this connection, it will also be recognized that yarns having characteristics equivalent to the yarns used in described, improved fabric constructions, would be within the spirit and scope of the present inventive concepts.

It will also be noted that woven fabric constructions are defined by the number of ends (warp yarns) and picks (fill yarns) per inch. Consistent, or repeatable, accurate measurement of the number of ends and picks in a fabric construction is obtained by employing the method defined in ASTM D-377C. For the sake of brevity the number of ends and picks will be given, without further specifying that such is a "per inch" number.

Similarly ASTM D-1777, used herein, provides accurate, repeatable measurement of fabric thicknesses.

Commercial versions of the '667 have the following construction:
  warp yarns: false twist 70/34
  fill yarns: false twist 70/34
  ends: 146
  picks: 85
  finish: hydrophobic surface finish (fluorocarbon)
  weight: 2.47 ounces per square yard
  thickness: 0.004 inch
  Calendering: "Heavy"

This '667 fabric also has the following barrier/permeability properties:

| Water Resistance: Hydrostatic Pressure Test, AATCC[1]-127-80 (Suter) | 60–75 (70 Average) |
| Water Repellency: Spray Test AATCC 22-1980 | 100 |
| Oil Repellency: Hydrocarbon Resistance Test, INDA[2]-80.8 | 4 |
| Alcohol Repellency INDA-80.9 | 7 |
| Water Resistance: Impact Penetration AATC-42-1975 | .25–.50 gm |
| Air permeability FTM[3]-5450 | <1.0 cfm |

[1]American Association of Textile Chemists & Colorists
[2]International Nonwovens & Disposables Test
[3]Federal Test Method The '667 fabric was "qualified" on the basis that its Suter rating was maintained above a minimum of 50, subsequent to 100 sterile reprocessing cycles (actually only 75 cycles were required for "qualification". The Suter rating, after 100 sterile reprocessing cycles represents a reduction in the order of 28%–38%.

As discussed above, the '677 fabric is prone to having random "voids" which can be the cause of strikethroughs. Surgical gowns are also "qualified" as being reliable for a given number of reuses. When the '677 fabric is used to form a barrier panel, or at least a critical barrier panel, the panel must be comprised of two layers of the fabric, in order for the gown to be "qualified".

The '667 fabrics have a "hand" which is acceptable, but nonetheless quite distinctive from a "cotton hand", particularly in regards to its tactile feel. That is, the "hand" was smooth, reflecting a relatively low coefficient of friction.

This leads to a discussion to the relationship of calendering to "hand" and Suter rating.

Calendering essentially consists of passing a length of fabric between a pair of pressure rolls at least one of which is heated. When a woven polyester fabric is calendered, the fabric is compressed and its density increased as the interstices between the yarns and the filaments of the yarns are decreased. The elevated temperature of the roll or rolls assists in the compression of the fabric and "sets" the fabric in its compressed state.

The degree of compression is a function of the rate of feed of the fabric, the pressure exerted by the pressure rolls, their temperature, and the number of times the fabric is passed between pressure rolls. Thus calendering is a matter of degree.

It has been determined that Suter rating is a direct function of the degree to which the described fabrics were calendered. Hypothetically, if sufficient heat and pressure are employed, the fabric would be transformed into a solid film and, in essence, an ultimately high Suter rating would be obtained, limited only to the rupture strength of the resultant polyester film. The basic construction of the '667 fabrics is thus capable, through calendering, to provide virtually any Suter rating that might be desired.

However, a high Suter is not the sole criterion for the construction of a reusable surgical gown fabric. Such fabric also requires first that it be highly drapable and preferably have a tactile feel approaching or approximating that of a cotton fabric. When calendering is relied upon to obtain high Suter ratings, with the '667 fabric, the "hand" property of the fabric degrades. That is, with increased calendering, the fabric is stiffer and less drapable and has a smoother surface, as compared to the desired standard of a "cotton hand".

The described '667 fabric, in its uncalendered state, possesses a "hand" which is readily distinguishable from the desired "cotton hand". In order to obtain the desired Suter ratings for the fabric, it was necessary to employ what is herein referenced as a "heavy" calendering. When heavily calendered, the '667 had a "hand" which is even more readily distinguishable from a "cotton hand". While this discussion focuses on the deficiencies in the "hand" of the '667 fabrics, it is, nonetheless, to be recognized that the "hand" of these fabrics was superior to that of disposable fabrics having corresponding barrier properties. In other words, the "hand" of the '667 fabrics was commercially acceptable.

It will also be briefly noted that there are other inherent advantages in surgical gown fabrics constructed of continuous filament, polyester yarns. Of particular interest is that linting and pilling (formation of filament "balls") during use is minimized. Thus there is a minimum likelihood of contamination of a surgical site by such foreign matter.

There has been an earlier effort to provide an improved, reusable surgical fabric of the type disclosed in the '667 patent and based on the teachings of parent application Ser. No. 546,354. This involved the following construction (identified as "modified" '667 fabric):
  warp yarns: false twist 70/34, set polyester yarn
  fill yarns: flat trilobal 70/88 polyester yarn (See Example 3 for details of "trilobal" yarn)

| greige fabric | finished fabric |
|---|---|
| ends: 138 | ends: 160 (nominal) |
| picks: 85 | picks: 86 (nominal) | finish: hydrophobic surface finish (fluorocarbon)
  weight: 2.6 ounces per square yard
  thickness: 0.004 inch
  Calendering: "Heavy"

The modified '667 fabric also has the following barrier/permeability properties:

| Water Resistance: Hydrostatic Pressure Test, AATCC[1]-127-80 (Suter) | 120 |
| Water Repellency: Spray Test AATCC 22-1980 | 90 |
| Oil Repellency: Hydrocarbon Resistance Test, INDA[2]-80.8 | 7 |
| Alcohol Repellency INDA-80.9 | 4 |
| Water Resistance: Impact Penetration AATC-42-1975 | .25–.50 gm |
| Air permeability | <1.0 cfm |

-continued

FTM[3]-5450

[1]American Association of Textile Chemists & Colorists
[2]International Nonwovens & Disposables Test
[3]Federal Test Method Compared to the '667 fabric, the modified '667 fabric exhibited a significantly increased Suter rating. However, its "hand" was quite similar to the "hand" of the '667 fabric and did not posses the desired "cotton hand".

Further, the modified '667 fabric did not completely overcome the problem of random breakdowns in the barrier function, discussed above, and, likewise, was used in a two layer construction in order to give adequate assurance that its barrier function would not be compromised.

There is one other pertinent, barrier fabric presently known. This is a fabric produced in Europe, the particulars of which have been derived, as best as could be done, from an examination and testing of samples thereof. It is understood that this fabric has been employed in the fabrication of reusable surgical gowns.

The construction of the European fabric is believed to be:
warp yarns: flat 120/80 polyester
fill yarns: false twist 168/250
ends: 159
picks: 82
finish: hydrophobic surface finish (fluorocarbon)
weight: 4.4 ounces per square yard
thickness: 0.009 inch
Calendering: "Light"

This European fabric also has the following barrier-/permeability properties:

| | |
|---|---|
| Water Resistance: Hydrostatic Pressure Test, AATCC[1]-127-80 (Suter) | 53 |
| Water Repellency: Spray Test AATCC 22-1980 | 100 |
| Oil Repellency: Hydrocarbon Resistance Test, INDA[2]-80.8 | 5 |
| Alcohol Repellency INDA-80.9 | 2 |
| Water Resistance: Impact Penetration AATC-42-1975 | N/A |
| Air permeability FTM[3]-5450 | 6.1 |

[1]American Association of Textile Chemists & Colorists
[2]International Nonwovens & Disposables Test
[3]Federal Test Method Sufficient quantities of the European fabric were not available to fully develop its properties.

However, it can be concluded that the European fabric would not be capable of providing a Suter rating in the order of 50 after 100 sterile reprocessing cycles in view of the fact that its initial Suter rating was only 53.

The "hand" of the European fabric does represent an improvement over the '667 fabric in more closely approximating the desired "cotton hand".

It is reasonable to assume that Suter of the European could be increased to a point where a rating of 50 would be maintained after 100 sterile reprocessing cycles. However, it is also reasonable to conclude that, if such were done, the "hand" of the European fabric would degrade to a point where it represented little or no improvement over the '667 patent.

Due to the small quantity of European fabric available, it was not possible to evaluate its tendency be subject to random breakdowns in the barrier function. There was insufficient fabric to construct a gown, as well as insufficient material to make a meaningful evaluation of the presence of "voids" in the fabric in a finished condition.

However, it is noted that the air permeability of the fabric is some sixfold greater than that of the '667 fabric. This leads to the conclusion that, with the European fabric construction, the presence of "voids" is to be expected and that it could not be reliably used in a single layer in forming a barrier panel.

It is also to be noted that this fabric's resistance to oil was significantly lower than that of the '667 fabric and modified '667 fabric and less than that required for "Qualification".

With the foregoing in mind, a broad object of the present invention is to provide an improved fabric construction which enables the attainment of higher Suter ratings, while at the same time providing a "hand" more closely approximating a "cotton hand".

Ancillary to and resultant from attaining such ends are the further objects of reducing the per use cost of reusable surgical gowns and other surgical/medical products requiring barrier properties.

Another object of the present invention is to provide improved methods for attaining the foregoing ends.

In brief summary, the foregoing ends are broadly attained by a reusable surgical/medical fabric capable of sterile reprocessing, which incorporates several features of construction, in various combinations, that contribute to improved barrier properties, or to providing an improved "hand", or to both.

These constructional features include the use of microdenier yarns in at least the fill yarns of the fabric, with the warp yarns having a denier to filament ratio no greater than about 2.5. In one preferred construction, the warp yarns are a false twist yarn having a denier to filament ratio of approximately 1.0 and the fill yarns are air textured core and effect yarns having a denier to filament ratio no greater than 1.0 and preferably in the range of 0.6. In another preferred construction, the warp yarns are trilobal yarns. In another preferred construction the warp yarns are double ended false twist yarns, with the fill yarns being false twist yarns.

Another feature is found in a fabric construction formed at least in part by microdenier yarns and having a porosity of at least $10 \times 10^6$ pores per square centimeter, and preferably at least about $13.0 \times 10^6$ pores per square centimeter; a mean pore size no greater than about $5.0\mu$ and preferably in the order $1.5\mu$ to $3.5\mu$; the maximum pore size is no greater than about $10.0\mu$ and preferably in the order of $4.0\mu$ to $8.0\mu$; and the minimum pore size is at least $0.8\mu$ and preferably in the order of $1.0\mu$ to $2.5\mu$.

Another feature is found in providing a filament density of at least about $2.0 \times 10^6$ filaments per cubic inch and preferably at least $3.8 \times 10^6$ filaments per cubic inch.

Other constructional features are found in a fabric thickness of at least 0.005 inch and advantageously in the order of 0.0055 inch to 0.008 inch, with a fabric weigh of at least 3.5 ounces per square yard and preferably in the order of 4.0 to 5.0 ounces per square yard.

Other features are found in a construction wherein the warp yarns have a relatively large crimp, the fill yarns have a relatively small crimp and the filaments of the warp yarns cover the major portions of the surfaces of the fill yarns and define the major portion of the surfaces of the fabric.

Further features of the invention are found in a twill weave fabric construction providing Suter ratings hitherto obtainable only from a plain woven fabric.

Other features of the invention are found in methods of manufacturing fabrics having the above features. Such features include "mechanically" working the greige fabric construction to increase its bulk. Preferably this is done through the use of a "jet dyeing machine" advantageously by using a "jet dyeing machine" to scour the greige fabric, i.e., remove sizing, or other dirt from the fabric.

Additionally, the high filament density of the present fabrics may be obtained by setting the number of ends in the finished fabric to a greater number than in the greige construction, preferably increasing the number of ends to about 160–170. The number of picks may also be set to an increased number. These ends are advantageously attained through the use of a tenter frame.

Other features of the invention are found in surgical gowns, surgical drapes and other surgical/medical items in which the foregoing fabrics are incorporated to form a barrier panel, preferable comprising a single layer of such fabrics.

The above and other related objects and features of the invention will be apparent from the following description of the fabrics which provide the stated ends, with specific Examples and the methods whereby they are made being set forth, with reference to the accompanying drawings, and the novelty thereof pointed out in the appended claims.

The teachings of the present invention will first be made through a description of the fabrication of preferred fabrics.

EXAMPLE 1

Figure 1:
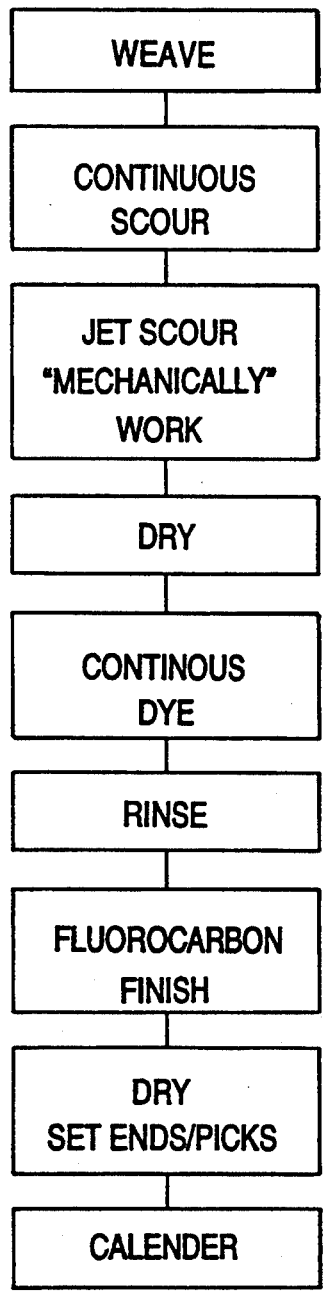
FIG. 1 is a block diagram of the method steps employed in making the fabric of Example 1.

Reference is made to FIG. 1 which illustrates the method steps employed in making the fabric of Example 1.

A piece of fabric having a length of some 200 yards and a greige width of approximately 72 inches, was woven on a standard air jet loom.

The greige (off the loom) construction was:
warp yarns: semi-dull false twist 100/100, set polyester yarn (bulked denier: 110) denier/filament: 1.0
fill yarns: air texturized core and effect 2/60/100, set yarn (bulked denier: 150) denier/filament: 0.6
ends: 153
picks: 75

At this point it will be noted that in a polyester fabric construction, at least the warp yarns are sized, viz., coated with a lubricating compound, to minimize breaking of filaments during weaving. Acrylic copolymers are commonly used as a sizing compound for polyester yarns. After weaving, the sizing and other contaminants must be removed. This is a cleaning process commonly known as scouring.

In this example, scouring was done as a two step process, comprising a continuous scouring and a batch process scouring. The continuous process, which is optional, comprised passing the length of fabric through a heated, aqueous detergent bath. The batch process involves the use of a "jet dyeing machine" in a jet scouring operation.

One of the features of the fabric of this example is that it is mechanically "worked" to further distort the yarns/filaments and increase the bulk of the fabric. This end is, advantageously, attained by employing a "jet dyeing machine" for the scouring process. Jet dyeing machines are well known and involve disposing a loop of fabric in a closed container. The fabric loop is fed in a controlled path, at rapid speeds, in which the loop is repeatedly flexed and folded in opposite directions in one portion of the loop and feed past a venturi induced liquid jet in another portion of the loop. When dyeing a fabric the liquid contains a dye. When employed to scour a fabric, the liquid contains a detergent/cleaning solution. Processing of fabrics in a jet dyeing machine is a "batch" process.

The machine employed for "jet scouring" was a Gaston County "Futura" machine. The temperature of the cleaning liquid was 280° F. and the time of treatment was three hours.

Polyester fabrics have an inherent characteristic of shrinking to increase bulk and density when immersed in a heated aqueous solution. The "mechanical" working of the fabric by "jet scouring" enhances the increase in bulk. This "mechanical" working of the fabric has also been identified as a contributing factor in attaining the desired "cotton hand" for the finished fabric, particularly as regards its tactile feel of being relatively rough, as found in cotton fabrics.

After scouring the fabric was then fed into a tenter frame and dried.

After scouring and drying, the fabric length was dyed by padding. This is a known, continuous process in which a length of fabric is fed through a bath and then through or between squeeze rollers. The bath comprises dyes for imparting the desired color to the fabric.

In dyeing polyester fabrics, problems are encountered in obtaining a uniform color density. To overcome this problem it is a common practice to employ leveling agents which have surfactant properties which have been identified as a cause for reducing the Suter ratings of finished fabrics (see related discussion in Example 2). The use of a continuous, padding dye process is preferred in that the leveling agents conventionally employed are more readily removed and/or do not adversely affect the Suter ratings of the finished fabric.

After dyeing, the fabric was rinsed in a continuous bath to make certain that there would be no contaminates which would adversely affect barrier properties.

Alternatively, a batch process could be employed. If a batch process, a jet dyeing machine can be employed to provide additional "mechanical" working of the fabric. Alternatively the scouring process could be carried out as a simple continuous process, with little or no "mechanical" working. Substantially all mechanical working would then be provided in the rinsing step through the use of a jet dyeing machine.

Rinsing is an optional step, dependent on the composition of the dye bath employed and the degree of assurance desired in assuring that the finished fabric will be free of contaminates which might adversely affect its Suter rating.

The dyed fabric, after rinsing was provided with a hydrophobic finish applied by padding. The padding bath comprised 8.75% Zonyl NWG (E. I. dupont) fluorocarbon, on a weight basis, with the balance being water.

The application of fluorocarbon finishes is known with prior art polyester fabrics and no problems were encountered in the application to the present fabric and in obtaining the desired hydrophobic property provided by this finish.

After application of the hydrophobic finish, the fabric was then dried in a tenter frame, which may receive the fabric directly from the continuous dyeing or continuous rinsing padding machine. A tenter frame is a known apparatus which feeds a length of fabric between infeed and outfeed rolls, while the side edges of the fabric are gripped to control its lateral width. These means enable the number of ends and picks in the finished fabric to be established. The tenter frame also includes means for heating the fabric and "setting" its construction to the desired number of ends and picks. (In the first described use of a tenter frame, it was simply employed to provide a drying function.)

In the present example the finished fabric construction was set to 162 ends and 76 picks, after discharge from the tenter frame.

The fabric was then calendered at a speed of 40 yards per minute using a single nip, between a heated steel roll and a fiber roll. The surface temperature of the steel roll was about 390° F. Calendering pressure was 90 tons. For purposes of definition with respect to the present invention, the described calendering parameters provided a "light" calendering.

The calendering operation further increases the density of the fabric and establishes its final thickness.

The fabric had the following finished construction:
ends: 162
picks: 76
weight: 4.1 ounces per square yard
thickness: 0.007 inch Samples of the finished fabric of Example 1 had the following barrier/permeability properties:

| | |
|---|---|
| Water Resistance: Hydrostatic Pressure Test, AATCC[1]-127-80 (Suter) | 80 |
| Water Repellency: Spray Test AATCC 22-1980 | 100 |
| Oil Repellency: Hydrocarbon Resistance Test, INDA[2]-80.8 | 5 |
| Alcohol Repellency | 10 |

-continued

| | |
|---|---|
| INDA-80.9 Water Resistance: Impact Penetration AATC-42-1975 | 0.02 gm |
| Air permeability FTM[3]-5450 | 0.82 cfm/ft$^2$ |

[1]American Association of Textile Chemists & Colorists
[2]International Nonwovens & Disposables Test
[3]Federal Test Method Samples of the finished fabric were provided to a panel of persons who tested and compared such samples with samples of cotton fabric of similar weight, pursuant to generally accepted methods of classifying the "hand" of fabrics. This was a "blind" test in that the panel made its evaluation without seeing the fabric. The consensus of the panel was that the "hand" of the defined fabric closely approximated, if not being essentially the same as, the "hand" of the cotton fabric, particularly as regards the tactile feel factor of a cotton "hand", which exhibits a perceptible resistance to movement of the fingers, as would be associated with a relatively high coefficient of friction.

The fabric of Example 1 provided initial Suter ratings at east as good as, and generally somewhat better than the '667 fabrics and a "hand" which was a marked improvement in essentially approximating a "cotton hand".

Samples of the Example 1 fabric were extensively examined and found to be free of pin holes.

As will be seen below, the fabric construction of Example 2 is essentially identical with that of Example 1. Testing of samples of Example 2 establish that this construction loses only 10%–20% in Suter rating when subject to 100 sterile reprocessing cycles. Thus the Suter rating of the fabric of Example 1 will be in the order of 64–72 after 100 sterile reprocessing cycles. Also based on the testing of the Example 2 fabric it is established that this fabric construction provides the same "cotton hand" after 100 sterile reprocessing cycles.

EXAMPLE 2

Several lengths of fabric were woven on a standard air jet loom, employing the same warp and fill yarns later employed in Example 1.

The greige construction of these lengths, having a width of approximately 72 inches, and woven on a standard air jet loom was:

warp yarns: semi-dull false twist 100/100, set polyester yarn (bulked denier: 110) denier/filament: 1.0
fill yarns: air texturized core and effect 2/60/100, set yarn (bulked denier: 150) denier/filament: 0.6
ends: 153
picks: 75

Each sample length of fabric in this example was processed in accordance with the method described in connection with Example 1, with the exceptions now to be discussed and as will be evident from FIG. 2.

The sample lengths were scoured by a continuous scouring process, as in Example 1.

After scouring, the samples were then dyed in a "batch process". In this Example the liquid employed comprised dyes and leveling agents normally employed in "jet dyeing" polyester fabrics. More specifically, this was done on a Gaston County "Futura" machine, employing a known dye bath, preferably at a temperature of 260° F. and a cycle time of three hours.

The "mechanical" working of the fabric to increase bulk was thus carried out in the "jet dyeing" step, as opposed to being done in the "jet scouring" step of Example 1.

In drying the fabric in a tenter frame, prior to calendering, the number of ends were set between 162 and 166 (164 average) and the number of picks was set between 76 and 86 (82 average). (No discernable difference were observed in the finished fabrics, which were attributable to these variations.)

The calendering operation also varied in that the fabric samples were fed through a double nip arrangement between two heated steel rolls at a rate of 20 yards a minute. The roll temperature was 380° F. and the roll pressure was 90 tons. This produced what is herein referenced as a "heavy" calendering.

The finished fabric samples of this example all had a weight of approximately 4.1 ounces per square yard and a thickness of approximately 0.007 inch.

The sample lengths were found to have the following properties:

| | |
|---|---|
| Water Resistance: Hydrostatic Pressure Test, AATCC[1]-127-80 (Suter) | 55–70 (63 Average) |
| Water Repellency: Spray Test AATCC 22-1980 | 100 |
| Oil Repellency: Hydrocarbon Resistance Test, INDA[2]-80.8 | 5 |
| Alcohol Repellency INDA-80.9 | 10 |
| Water Resistance: Impact Penetration AATC-42-1975 | .03 gm |
| Air Porosity (Gas Permeability) FTM[3]-450 | <1.0 cfm/ft$^2$ |

[1]American Association of Textile Chemists & Colorists
[2]International Nonwovens & Disposables Test
[3]Federal Test Method The samples of this example were evaluated, as indicated above, and found to have a "hand" which was very similar to a cotton "hand". This is similar to the "hand" possessed by the fabric of Example 1.

The sample lengths of Example 2 were made up into surgical gowns, which were then subject to 100 sterile reprocessing cycles. After these sterile reprocessing cycles, the fabric was again tested. It was found that the initial properties of the fabric were virtually unchanged, with the exception that the Suter ratings had been reduced to approximately 10%–20%. The variations in Suter degradation are attributable to differences in the details of the sterile reprocessing cycles to which they were subjected in testing.

It is also to be noted that the desired "hand" of the sterile reprocessed fabrics was unaffected after 100 cycles.

A further feature of the sample lengths of this Example is the absence of "voids". As previously indicated there is no practical, let alone a standard test for "voids". The sample lengths of this example were extensively examined, before and following 100 sterile reprocessing cycles without any "voids" being identified. The procedure employed has been successful in identifying "voids" in the '667 fabric, thus there is a reasonable assurance that this fabric is virtually free of "voids".

The surgical gowns in which the fabric if this Example was incorporated employed a single layer of fabric in the critical front panel of the gown. This is opposed to the generally accepted practice of employing two layers of the '667 fabric, for this gown portion, that is particularly subject to having liquids impinged thereon during a surgical procedure. These gowns were experimentally used during surgical procedures with the frequency of strikethroughs being no greater than one tenth of one percent of the number of uses. This verified both the effectiveness of the barrier properties of the fabric, as well as the virtual absence of "voids".

At this point, the relationship between Example 1 and Example 2 will be discussed. The sample lengths of Example 2 were produced prior to the fabric of Example 1. As is evident from the initial test data for Example 2, a considerable variation was found in Suter ratings, despite the fact that the fabrication process for each sample length was essentially the same.

This prompted a further evaluation of the fabrication process and led to identification of surfactants in the leveling agents, employed in the bath for the "jet dyeing batch process", as a cause of the Suter rating variation. More importantly, it was discovered, that when such wetting agents were eliminated from the fabric, a substantial increase of the Suter rating, was obtained without significant variations in the fabric constructions.

The process of Example 1 effectively eliminates the problem caused by leveling agents used in "jet dying". It is also possible that the use of different leveling agents could be employed in "jet" dyeing, to the end that the "mechanical" working of the fabric could be done in this step as well as in the scouring step. Likewise, "mechanical" working of the fabric could be an independent step, or combined with other steps in making the finished fabric.

EXAMPLE 3

A piece of fabric having a length of several yards and a greige width of approximately 72 inches, was woven on a standard air jet loom.

The greige (off the loom) construction was:
warp yarns: flat trilobal 100/50 polyester yarns denier/filament: 2.0
fill yarns: air texturized core and effect 2/60/100, set yarn (bulked denier: 150) denier/filament: 0.6
ends: 153
picks: 75

Figure 3:
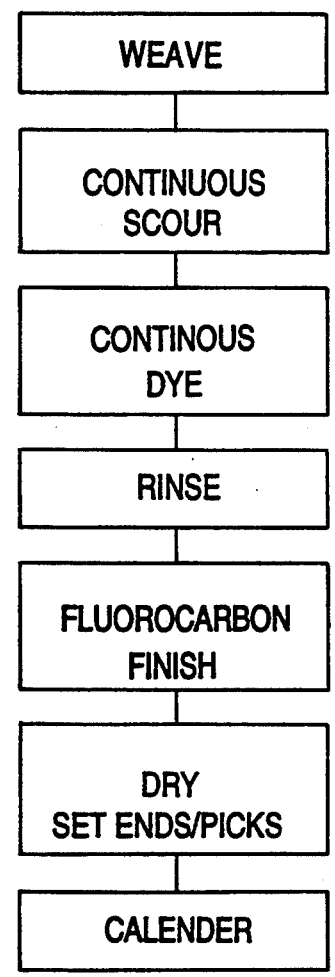
FIG. 3 is a block diagram of the method steps employed in making the fabric of Example 4.

The greige fabric was then processed in accordance with the method steps of FIG. 3. These steps are essentially the same as the method of Example 1 with the exception that the "jet scouring" step is eliminated (and with it the first drying step).

There are additional variations in that, prior to calendering, the ends were set at 166 and the picks were set at 77. Further, in the calendering operation, a "heavy" calendering was provided in the fashion described in connection with Example 2.

The weight of the finished fabric was approximately 4.0 ounces per square yard and its thickness was approximately 0.006 inch.

The fabric was tested and found to have the following properties:

| | |
|---|---|
| Water Resistance: Hydrostatic Pressure Test, AATCC[1]-127-80 (Suter) | 100 |
| Water Repellency: Spray Test AATCC 22-1980 | 100 |
| Oil Repellency: Hydrocarbon Resistance Test, INDA[2]-80.8 | 5 |
| Alcohol Repellency INDA-80.9 | 10 |
| Water Resistance: Impact Penetration AATC-42-1975 | .01 gm |

| Air Permeability | <1.0 cfm |
| FTM³-5450 | |

[1]American Association of Textile Chemists & Colorists
[2]International Nonwovens & Disposables Test
[3]Federal Test Method The "hand" of the fabric was evaluated, as before, and found to be significantly closer to a cotton "hand" than the '667 fabric. However, the "hand" of this fabric was not quite as good as that of Examples 1 and 2 in that its tactile feel was slightly smoother.

The fabric was also evaluated and found to be free of "voids", thus making it suitable to be employed as a single thickness in the fabrication of surgical gowns.

Based on the testing of samples in Example 2, this fabric will predictably lose no more than 10% to 20% of its initial Suter rating when subject to 100 sterile reprocessing cycles and its other properties will not be degraded to a point where the fabric is unsuitable to provide the necessary barrier functions for a surgical gown.

The fabric of Example 3 represents a significant improvement in surgical gown fabrics in having a significantly increased Suter rating and a significantly improved "hand". The fabric of Example 3 is more economical to produce because of the use of a warp yarns having a higher denier to filament ratio.

fill yarns: false twist 150/200, set polyester yarn (bulked denier: 165 denier/filament: 0.75
ends: 147
picks: 72

Figure 2:
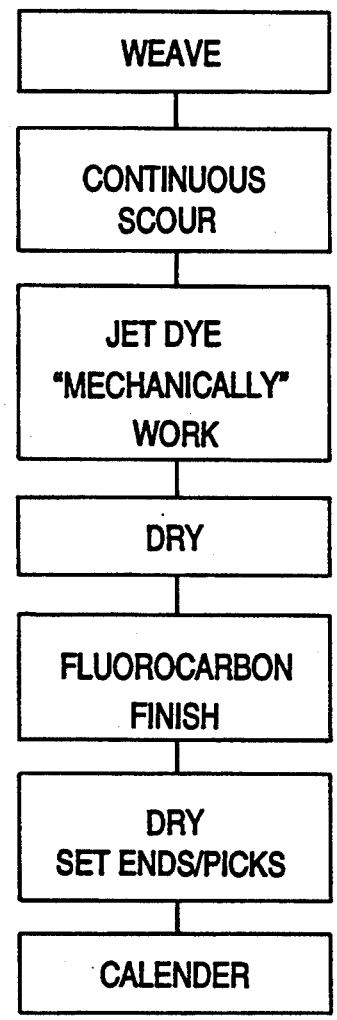
FIG. 2 is a block diagram of the method steps employed in making the fabric of Examples 2 and 4.

The greige fabric was then processed in accordance with the method steps of FIG. 2. These steps are essentially the same as the method of Example 2. Prior to calendering, the ends were set at 160 and the picks at 82.

The weight of the fabric was 4.2 ounces per square yard and its thickness approximately 0.008 inch.

The fabric was tested and found to have the following properties:

| Water Resistance: Hydrostatic Pressure Test, AATCC[1]-127-80 (Suter) | 79 |
| Water Repellency: Spray Test AATCC 22-1980 | 100 |
| Oil Repellency: Hydrocarbon Resistance Test, INDA[2]-80.8 | 5 |
| Alcohol Repellency INDA-80.9 | 10 |
| Water Resistance: Impact Penetration AATC-42-1975 | .06 gm |
| Air Permeability FTM³-5450 | <1.0 cfm/ft² |

[1]American Association of Textile Chemists & Colorists
[2]International Nonwovens & Disposables Test
[3]Federal Test Method

TABLE

| Fabric | Ends | Warp Fil'nts | d/f[A] | Picks | Fill Fil'nts | d/f[B] | Thick (in.) | Filament Density (Fil/in³ × 10⁶) | Suter | Avg. Min Pore (μ)[c] | Avg. Max. Pore (μ)[c] | Mean Pore Size (μ)[c] | Pore Density Pores/cm² × 10⁶[c] |
|---|---|---|---|---|---|---|---|---|---|---|---|---|---|
| '667 | 146 | 34 | 2.06 | 85 | 34 | 2.06 | .004 | 1.96 | 70 | 4.36 | 12.0 | 5.78 | .72 |
| Mod. '667 | 160 | 34 | 2.06 | 86 | 68 | 1.03 | .004 | 2.82 | 120 | | | | |
| European | 159 | 80 | 1.5 | 82 | 250 | .67 | .009 | 3.69 | 53 | 5.18 | 22.4 | 7.58 | 2.03 |
| Ex. 1 | 162 | 100 | 1.0 | 76 | 200 | .6 | .007 | 4.49 | 80 | 1.92 | 7.06 | 2.64 | 19.0 |
| Ex. 2 | 162 | 100 | 1.0 | 76 | 200 | .6 | .007 | 4.49 | 63 | | | | |
| Ex. 3 | 166 | 50 | 2.0 | 77 | 200 | .6 | .006 | 3.95 | 100 | 1.25 | 4.31 | 2.07 | 15.1 |
| Ex. 4 | 163 | 68 | 1.47 | 74 | 200 | .75 | .008 | 3.24 | 80 | 2.03 | 6.41 | 2.94 | 13.6 |

[A]Dennier to filament ratio of warp yarns.
[B]Dennier to filament ratio of fill yarns.
[c]Pore and porosity measurements were made on a "COULTER" "POROMETER II" Analyzer, manufactured by Coulter Electronics Limited, Luton, England. Software provided with this analyzer (Part Number 9909858) employed an automated and extended version of the liquid displacement method defined in ASTM F316-80 (1980)

An important feature of this fabric is the use of trilobal warp yarns. Trilobal yarns differ from more commonly used yarns in that they are formed of filaments having a generally triangular cross section (See FIG. 7). Trilobal yarns are commercially available from such synthetic yarn producers as E. I. dupont and are used for apparel fabrics to provide an aesthetic, reflective affect.

The use of trilobal yarns enhances yarn density and Suter ratings, with a minimum adverse affect on the "hand" of the fabric. It further permits such end to be attained without "mechanically" working the fabric to increase its bulk, as was done in Examples 1 and 2. It further facilitates the scouring step. These factors, in combination with a relatively low yarn cost, all combine to make this fabric an economical surgical gown fabric.

EXAMPLE 4

A piece of fabric having a length of several yards and a greige width of approximately 72 inches, was woven on a standard air jet loom.

The greige (off the loom) construction was:
warp yarns: false twist 2/34/50 set polyester yarns denier/filament: 1.47 bulked denier: 110

The "hand" of the fabric was evaluated, as before, and found to be significantly closer to a cotton "hand" than the '667 fabric. The "hand" of this fabric was substantially the same as the hand of the fabric of Example 3.

The significance of this fabric is found in its superior Suter rating as compared to that of Example 2. Bearing in mind that the Suter ratings of both Example 2 and Example 4 where compromised by residual leveling agents in the finished fabrics, it will be appreciated that the construction of Example 2 gives an increased Suter rating.

It will be noted that this fabric was also found to be free of "voids".

This fabric is of particular significance in providing an even greater potential for significantly increasing the number of permitted reuses and thereby decreasing the per use cost of reusable surgical gowns.

The advantages of this fabric construction (employing a two ended, false twist warp yarn and a single ended false twist fill yarn) was further demonstrated by a modified fabric construction which was manufactured in the same fashion as that just described, with the exception that it was a twill weave as opposed to a plain weave. The number of picks in the greige construction was also increased from 75 to 82.

The barrier properties, particularly as regards Suter rating, of the twill fabric were comparable to those of the fabric of Example 2. This is construction enables to provision of reusable surgical gown fabrics having a "patterned" surface, as provided by the twill weave. Such patterned surface is desirable in for aesthetic purposes, as well as providing visual indicia for the items formed with the twill fabric. The twill pattern also gives the perception of a cotton like "hand" if not actually providing a "hand" that more closely approximates a "cotton hand".

A twill weave, as herein contemplated, is a fabric characterized by diagonal lines (ribs) on the surface of the fabric. These lines are produced by staggered "floats", which are produced by fill yarns passing over a plurality of warp yarns. It is preferred to employ a $2 \times 1$ twill weave wherein the fill yarns pass over 2 warp yarns in forming each float. It will also be noted that a twill weave construction can provide ribs on one or both surfaces of a fabric. It is also to be appreciated that there is a broken twill construction in which the ribs run to the right and then to the left. This weave, also known as a herringbone weave, falls within the definition of "twill weave" and can also be employed.

The finished twill woven version of Example 4 had an initial Suter of 65, a weight of 4.5 ounces/square yard, and a thickness of 0.007 inch, with 160 ends and 91 picks. The Suter rating of this twill fabric was 65. This Suter was also adversely affected by leveling agents, as discussed above and in connection with Example 2.

In a broad sense the improved fabrics are attained by a highly bulked, tightly woven fabric construction. The features of this construction will now be discussed with reference to the following Table, which also provides available data relevant to prior art fabrics:

It will be apparent that the fabrics of the present invention structurally distinguish the prior art fabrics by these porosity characteristics. Thus it is preferred that the average minimum pore size be at least about $0.8\mu$ and preferably in the order of $1.0\mu$ to $2.5\mu$, the average maximum pore size be no greater than about $10.0\mu$ and more specifically in the order of $4.0\mu$ to $8.0\mu$, with the mean pore size being no greater than $5.0\mu$ and preferable in the order of $1.5\mu$ to $3.5\mu$.

Further, it is preferred that the pore density be at least $10 \times 10^6$ pores cm$^2$.

These pore sizes are advantageously employed in a fabric construction having a filament density of at least $2.0 \times 10^6$ filaments per cubic inch. Filament Density is the product of the number of ends times the number filaments in a warp yarn plus the product of the number of picks time the number of filaments in a fill yarn, divided by the thickness of the fabric. It is further preferred that this filament density be provided in a fabric having a thickness no less than about 0.006 inch.

The fabrics of Examples 1, and 3 have in common a significant increase in barrier properties, particularly as measured by resistance to a static water head, viz, the Suter rating attained.

The fabric of example 4 exhibits a significant improvement in Suter rating over the fabric of Example 2 (both of which were manufactured in essentially the same fashion). This indicates that advantages can be had in employing a two ended yarn as the warp yarn in the fabric construction. It also indicates that a false twist texturized yarn can be employed advantageously as fill yarns in place of the preferred air texturized, core and effect, texturized fill yarn. The effectiveness of a double ended warp yarn is also evidenced by the improved Suter rating obtained by the Example 4 fabric over the European fabric. These two fabrics are quite similar in denier to filament ratios and filament density. However, the Example 4 fabric has a superior Suter rating, which is also reflected in the porosity measurements.

This leads to a consideration of the denier to filament ratio parameter. It is preferred, for purposes of providing a "hand" most closely approximating, if not indistinguishable from a "cotton hand" that both warp and fill yarns be textured, microdenier yarns, i.e. a yarn having a filament to denier ratio of less than approximately 1.0. However, so long as at least one of the yarns (warp or fill) is a textured microdenier yarn, the advantages of the present invention can be realized. Preferably the fill yarns are air textured, core and effect microdenier yarns.

The fabric of Example 3 also demonstrate that barrier properties (Suter ratings) can be improved through the use of untextured, trilobal warp yarns, with "hand" improvement provided through the use of air texturized, core and effect fill yarns.

The structural distinctions of the present fabrics is further illustrated by the photomicrographs of FIGS. 4-7. Corresponding photomicrographs of the prior art '667 fabric are found in FIGS. 9 and 10.

Figure 5:
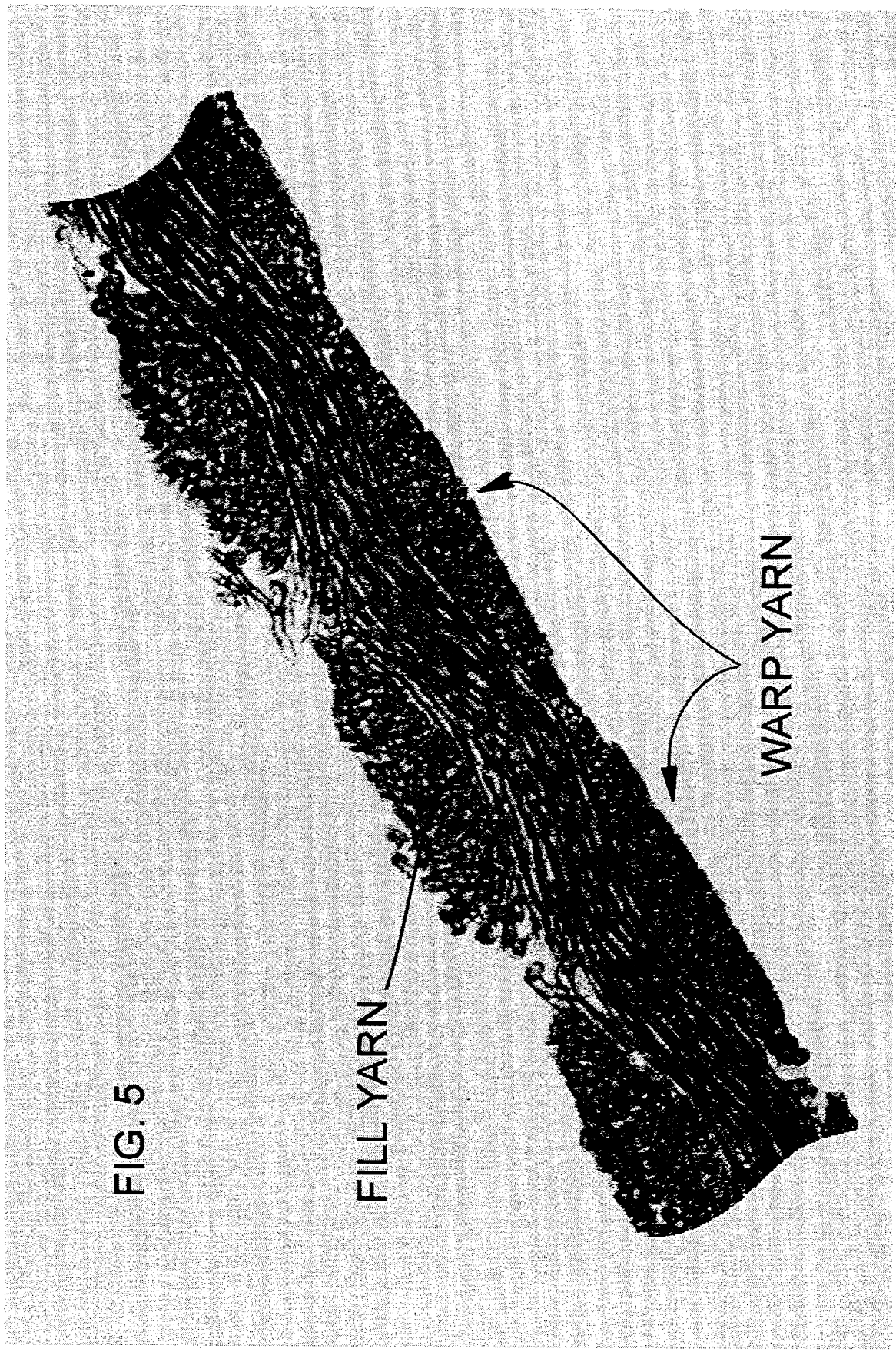
FIG. 5 is a photomicrograph taken longitudinally of a fill yarn and showing the warp yarns in cross section, taken on line 5—5 in FIG. 4 (of a lightly calendered sample of Example 1)
Figure 7:
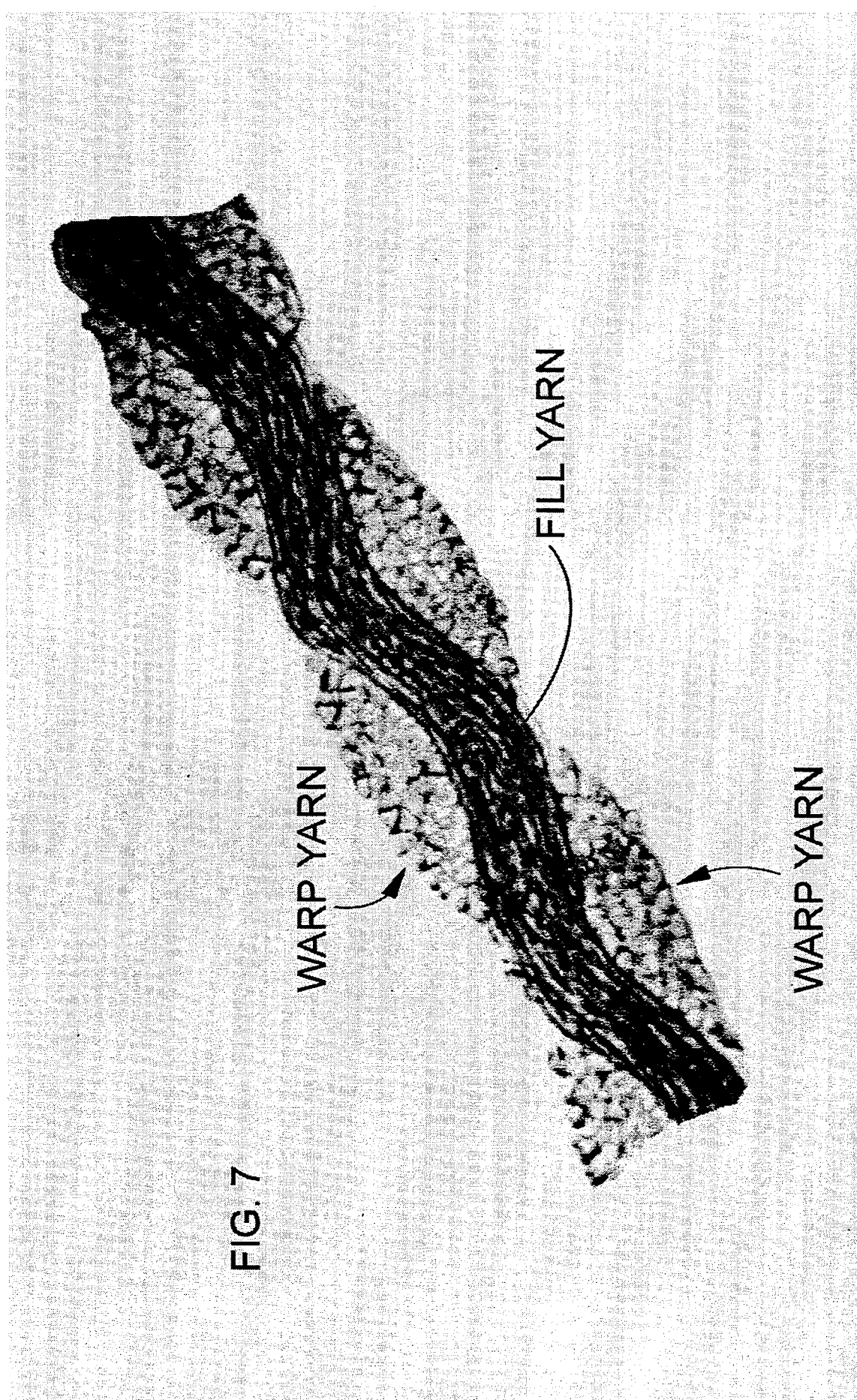
FIG. 7 is a photomicrograph taken longitudinally of a fill yarn of the fabric of Example 3 and showing the warp yarns in cross section.
Figure 9:
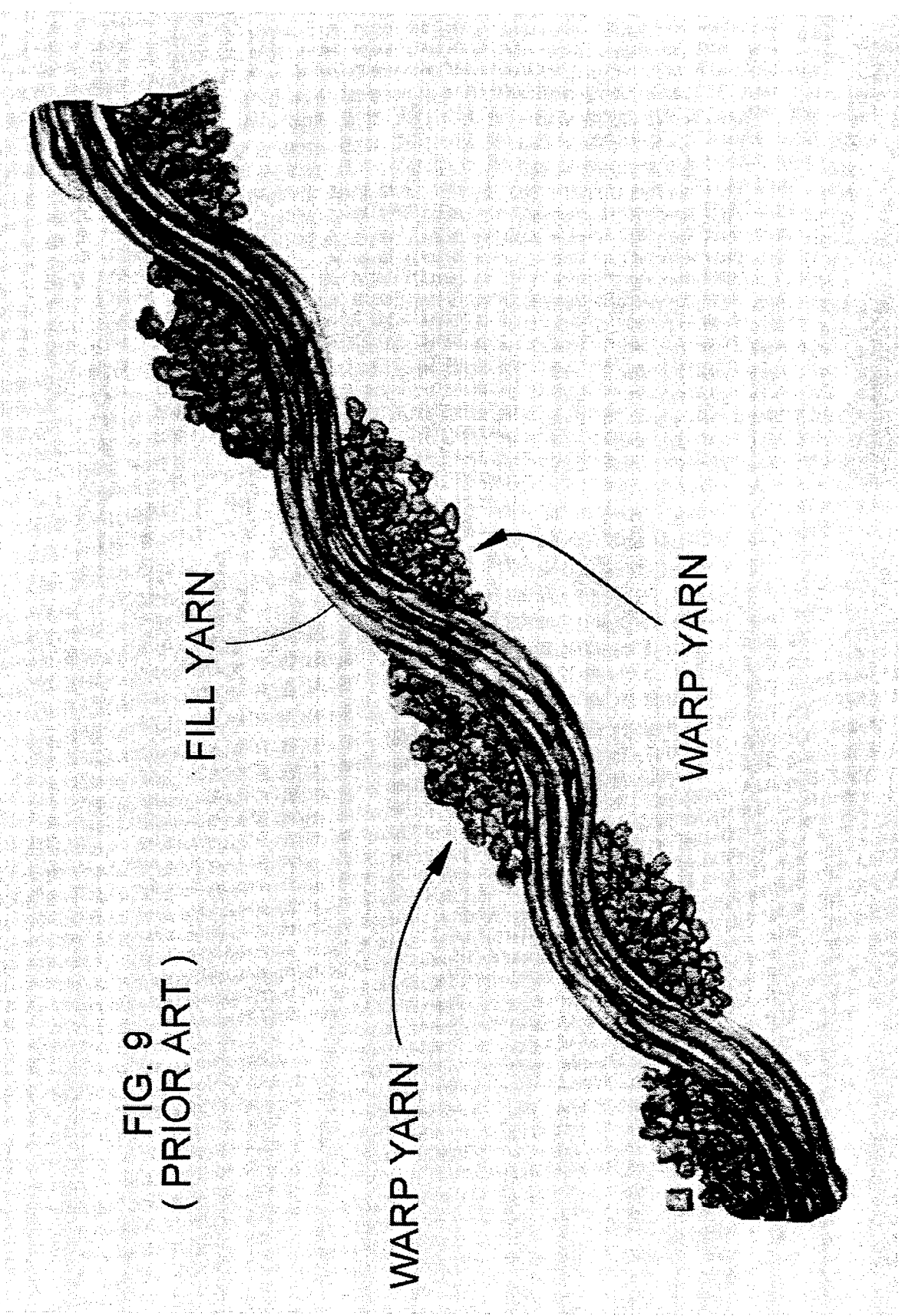
FIG. 9 is a photomicrograph taken longitudinally of a fill yarn of the prior art '667 fabric and showing the warp yarns in cross section.
Figure 10:
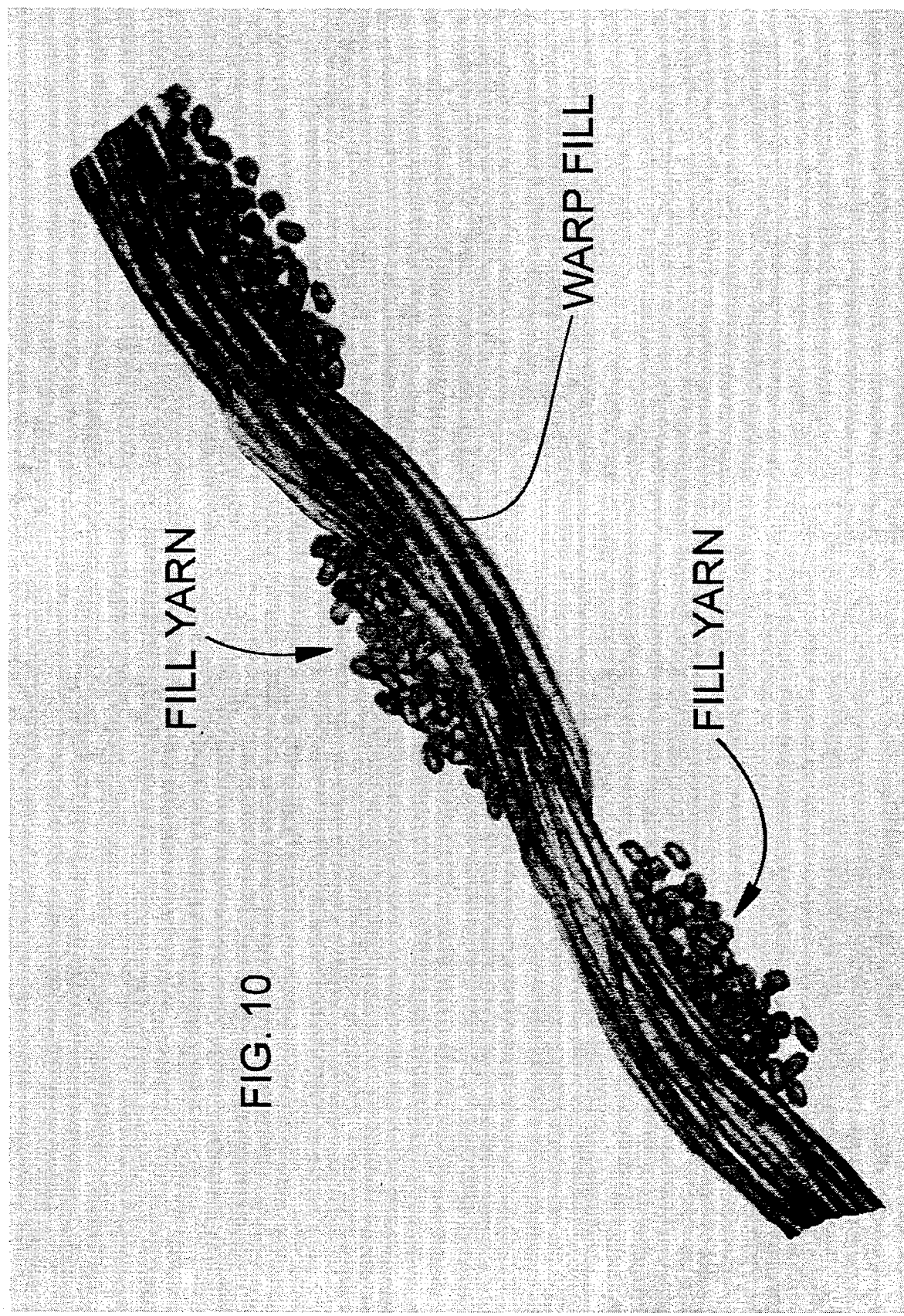
FIG. 10 is a photomicrograph taken longitudinally of a warp yarn of the prior art '667 fabric and showing the fill yarns in cross section.

A preferred construction feature is apparent from a comparison of FIGS. 5 and 7 with FIG. 9. This illustrates that the fill yarns have a relatively low crimp relative to the crimp of the fill yarns of the '667 fabric. Further, filaments of the warp yarns are displaced to cover something in the order of 80%, or more (in Example 1 the coverage approaches 100%) of the portion of the fill yarns that define the outer surface of the fabric.

Figure 8:
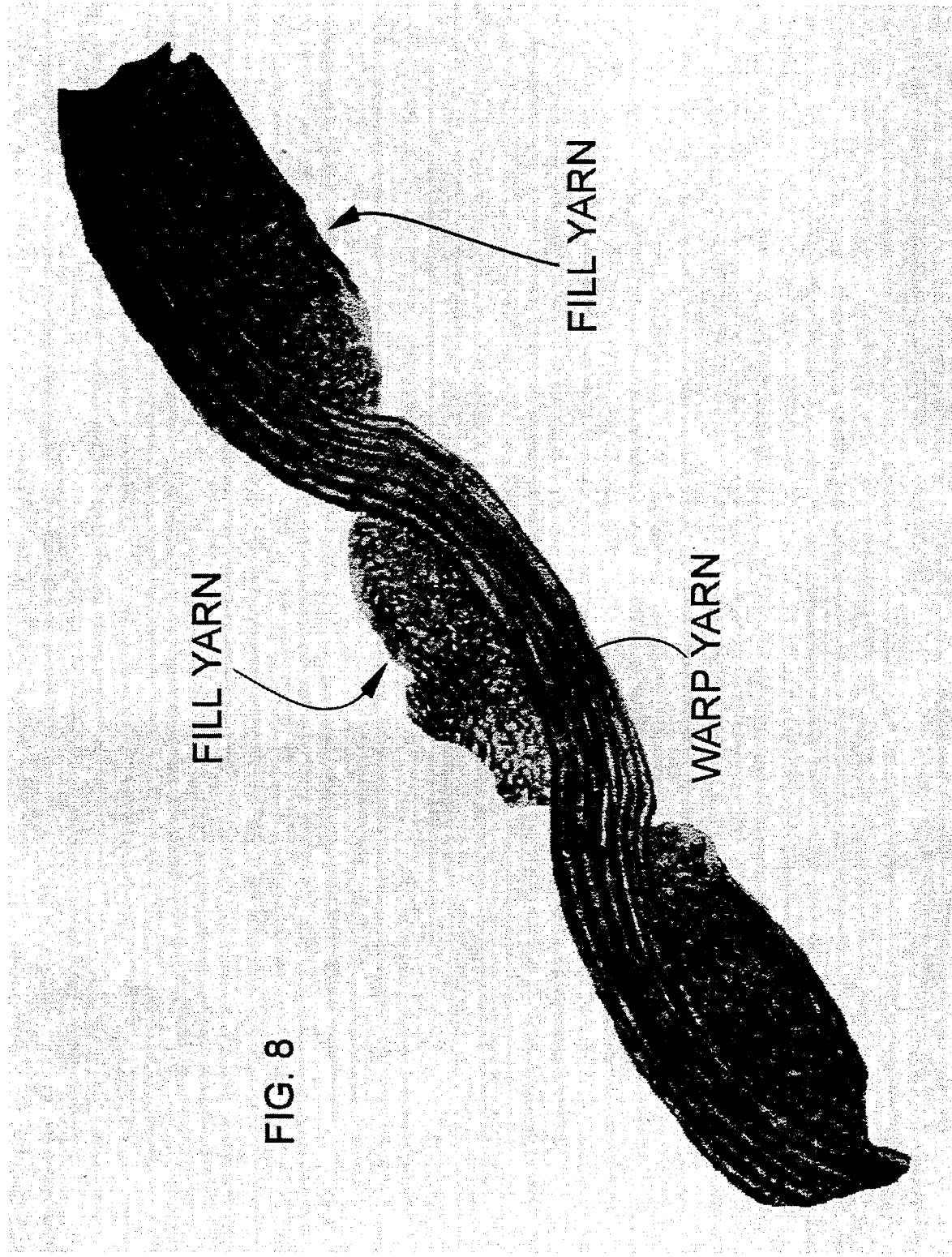
FIG. 8 is a photomicrograph taken longitudinally of a warp yarn of the fabric of Example 3 and showing the fill yarns in cross section.

A comparison of FIGS. 8 and 8 illustrates a converse relationship in that the warp yarns of the present invention are crimped to a relatively large extent, as compared to the crimp of the prior art, '667 fabric.

Figure 4:
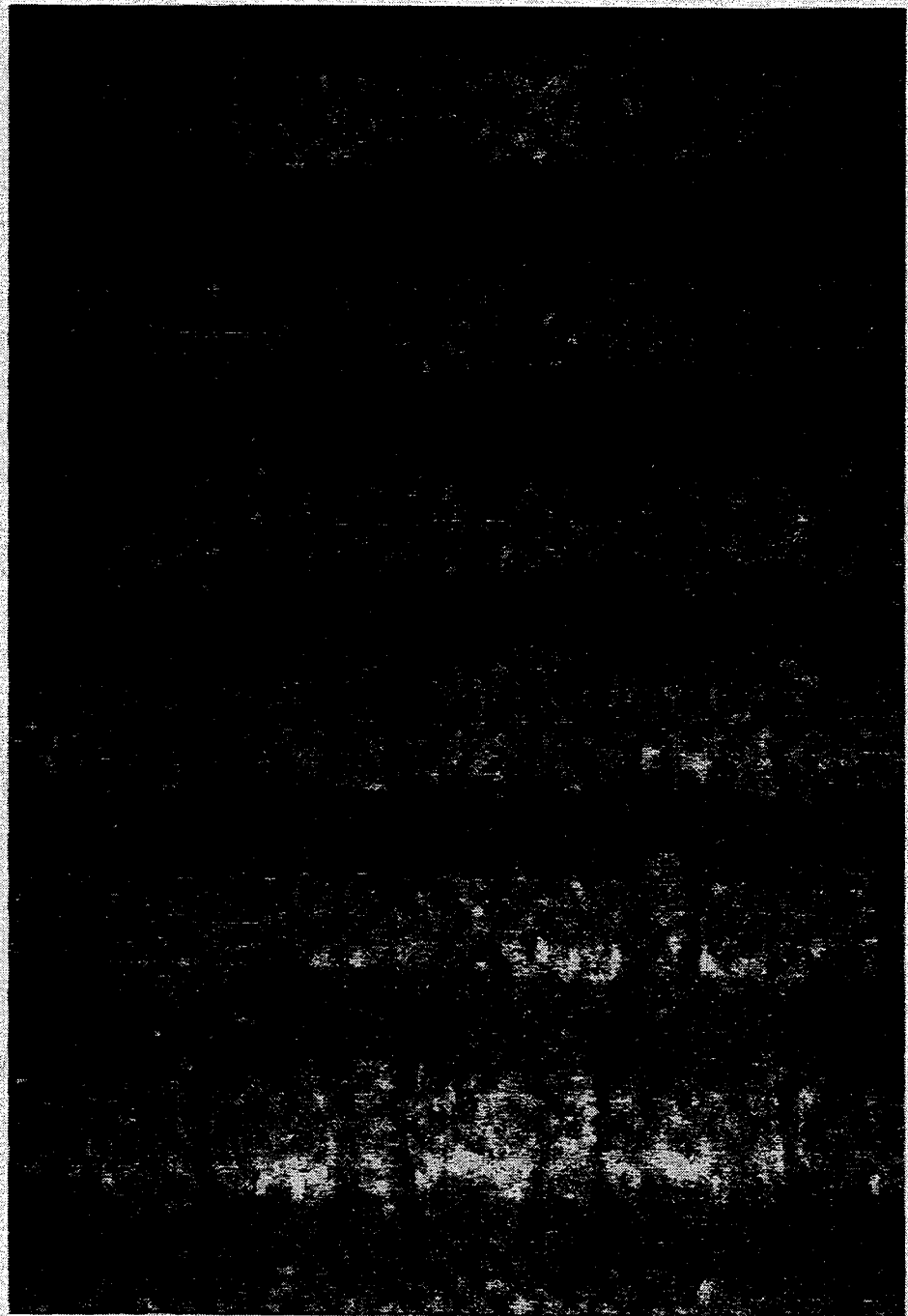
FIG. 4 is a photomicrograph of the surface of the fabric of Example 1 (uncalendered)
Figure 6:
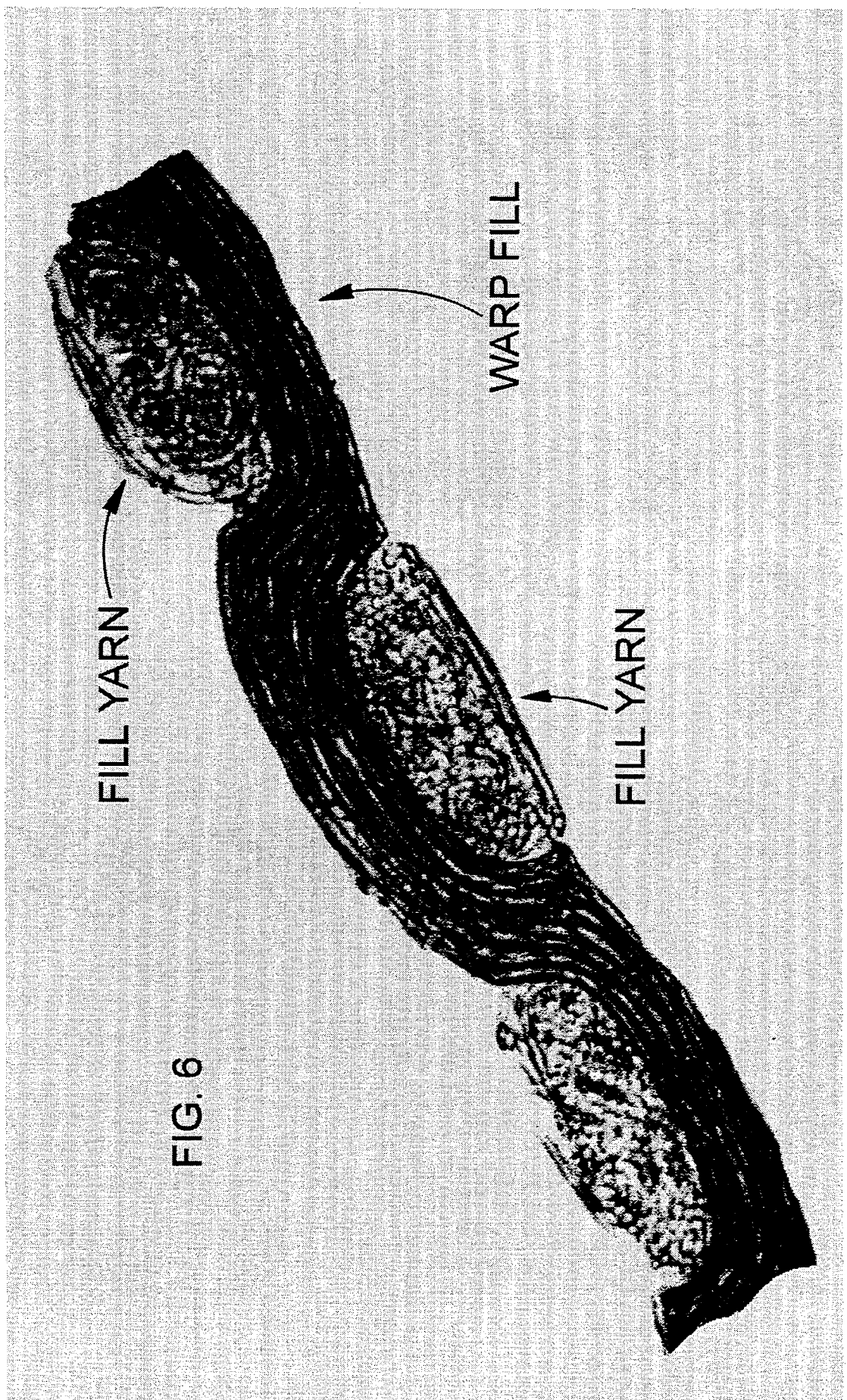
FIG. 6 is a photomicrograph taken longitudinally of a warp yarn and showing the fill yarns in cross section, taken on line 6—6 in FIG. 4 (of a lightly calendered sample of Example 1)

It is to be noted that the photomicrographs do not illustrate the precise construction of the fabrics of examples described in connection with Examples 1 and 3, insofar as calendering is concerned. FIG. 4 illustrates the fabric of Example 1 in an uncalendered condition. FIGS. 5 and 8 illustrate the fabric of Example 1 with "light" calendering. FIGS. 4 and 5 illustrate that the coverage of the fill yarns by the filaments of the warp yarns is obtained in the calendering process and is effectively obtained when "light" calendering is applied. FIGS. 6 and 7 illustrate the fabric of Example 3 with a light calendering and illustrate the tightly packed construction obtained with a "light" calendering, as well as with a "heavy" calendaring.

It is to be remembered that the requisite barrier properties for surgical gown fabrics is dependent on the fabric having a hydrophobic surface finish. The provision of a hydrophobic surface finish to polyester fabrics is well known. Further, providing a hydrophobic finish is not affected by using different forms of polyester yarn in the fabric construction. Thus, for example, the use of microdenier yarns does not restrict the ability to provide a hydrophobic surface finish.

Fluorocarbon surface finishes are a well known hydrophobic finish and their application to polyester fabrics to obtain a desired hydrophobic affect can be, and is, done routinely by those skilled in the art.

In a sense, the present fabrics provide an improved "carrier" for the hydrophobic surface finish.

Polyester, as a material is naturally hydrophobic. The hydrophobic finish enhances this characteristic to the point where it is sufficient to perform the desired barrier function. If this hydrophobicity could be otherwise be enhanced, as by some molecular modification, then the present fabric constructions could, likewise, provide improved Suter ratings and a "hand" similar to a "cotton hand".

These improved characteristics of the present fabrics provide two significant advantages.

First, the fabrics, more particularly the gowns fabricated therefrom, are capable of an increased number of reuses. Second, they can reliably provide effective barrier protection when used as a single layer, as opposed to the prior practice of employing a double layer of fabric where the hazards of a strikethrough are critical.

The fabrics of all Examples of the invention provide the further advantage of having a "hand" which is a significant improvement over the "hand" of the '667 fabric, with the "hand" of Examples 1 and 2 attaining the desired end of a "hand" which is quite similar to, if not virtually indistinguishable from, the "hand" of a cotton fabric of similar weave and weight.

At this point it will be noted that in weaving high density fabrics, the designs inherently enable the incorporating a greater number of ends than picks. Also, the cost of adding additional picks is greater than that of adding additional ends. Thus it is conventional for the weight of high density fabrics to be comprised of approximately 60% warp yarns and approximately 40% fill yarns. Because of these characteristics, the same general weight ratio is found in the fabrics of the present invention. That is also to say that the fabrics of the present invention are capable of being woven on conventional looms.

As previously noted, the improved Suter ratings of the fabrics of the invention are, to a large extent, attributed to the extreme yarn density of the fabrics.

More specifically this yarn density is achieved by a construction having a finished round count of at least about 230, with one of the warp or fill yarns having a denier of at least 100 and the other of the warp or fill yarns having a denier of at least 120.

For purposes of being woven on a conventional loom, it is preferred that the number of ends be at least approximately 160 and the number of picks be at least approximately 70. Again the design limitations of conventional looms come into play in that it is difficult, if not impossible, to incorporate 160, or more, ends per inch. For this reason, in accordance with method aspects of the invention, it is preferred to weave a greige fabric having a lesser number of ends, preferably in the order of 147. The greige fabric is later "mechanically" finished through negative stretching to produce a finished fabric having 160, or more, ends. The same general conditions apply to the number of picks. This is to say that the greige fabric may contain a reduced number of picks, which is increased to the desired number for the finished fabric, through "mechanical" finishing.

All prior reusable surgical gown fabrics, or at least all such fabrics which are known to have had any substantial commercial acceptance, have been of a plain woven (1×1) construction. Such plain woven construction is also preferred in the fabrics herein disclosed. However, as indicated in Example 4, other weaves may also be employed.

While densely bulked fabric constructions are well known for uses outside the surgical/medical field, a unique aspect of the present fabrics is that in addition to improved Suter ratings, they possess a "hand" which is virtually indistinguishable from a "cotton hand". While such end has been attained in apparel fabrics, it has not been achieved in reusable barrier fabrics suitable for surgical/medical purposes.

This end is attributable both to the preferred use of air texturized core and effect, microdenier (denier/filament≦1.0) fill yarn and to the mechanical working of the greige construction, as above discussed.

The improved barrier properties of the present fabric are also attributed to the micro-porosity of the fabric which is attained through the use of microdenier and near microdenier yarns, incorporated in a high density fabric construction.

The fabrics of the present invention permit the elimination of the calendering. This is to say that the intrinsic construction of the present fabrics, when uncalendered, provides barrier properties at least equivalent to those of the '667 fabric. Thus, it is possible, to reduce the cost of reusable surgical/medical fabrics having an improved "hand" and capable of use in a single layer in surgical gowns, which meet the standards for reuse.

While not detailed in the above discussions, it is to be remembered that all of the fabrics of the present fabrics possess the necessary barrier properties, other than water resistance (hydrostatic pressure—Suter). Further these properties are maintained at minimum required values and the Suter rating is degraded no more than the '667 fabric and in most cases no more than about 10%–20%, when subject to 100 sterile reprocessing cycles.

In the foregoing fabric constructions the air permeability has been a specific characteristic. It has been found that in the manufacture of fabrics, if the air permeability is no greater than 1.0 cfm/square yard, then the desired Suter has been obtained. It is primarily used as a quality control check on the calendering operation. However, desired Suter ratings can be obtained with higher air permeabilities.

It will also be noted that these constructions provide sufficient air permeability for comfort and steam permeability, notwithstanding that there is no specified minimum air permeability.

For the most part, the present invention has been described in connection with providing an improved, reusable, surgical gown fabric and surgical gowns made therefrom. It is to be recognized that there are other reusable articles which also require a reusable, barrier fabric meeting the same criteria as reusable surgical gown fabrics. A notable example is a reusable surgical drape. Other examples include work aprons, isolation gowns and wrappers for sterilized instruments.

The fabric of the present invention is thus more properly characterized as a reusable surgical/medical fabric.

It is also to be understood that the invention not only contemplates this improved fabric, but also surgical/medical articles, such as surgical gowns, surgical drapes and the like fabricated therefrom.

Those skilled in the art may well adopt modifications to the fabric constructions and methods herein described. Thus, for example, although not known at the present time, there could be a synthetic yarn developed which has substantially the same properties of the polyester yarns herein employed, and which would be an equivalent in constructing fabrics having the characteristics and advantages herein taught. Likewise, there could be improvements in looms which would enable variation from the specific teachings herein, while providing the benefits herein provided within the spirit of the present invention.

The scope of the present invention is therefore to be derived from the following claims.

Having thus disclosed the invention, what is claimed as novel and desired to be secured by Letters Patent of the United States is:

1. A method of making a reusable surgical/medical fabric capable of sterile reprocessing, comprising the steps of
    weaving a length of fabric having a greige construction which is plain woven with approximately 153 ends and 75 picks and
    further, in weaving the greige construction, employing continuous filament, multi-filament polyester yarns with
        the warp yarns being a false twist texturized 100/100 yarn having a bulked denier of approximately 110, and
        the fill yarns being a 2/60/100 air texturized, core and effect, yarn having a bulked denier of approximately 150,
    "jet scouring" the greige fabric to remove sizing and the like and to "mechanically work" the fabric to thereby further bulk the yarns and filaments of the fabric,
    feeding the scoured fabric through a dye bath to provide a desired color therefor,
    drying the fabric,
    treating the fabric in an aqueous bath comprising a fluorocarbon, hydrophobic agent to impart a hydrophobic finish to the fabric,
    drying the fabric and setting the number of ends to approximately 162 and the number of picks to approximately 76, then
    calendering the fabric by using a single nip between a steel roll heated to 390° F. and a fiber roll, at a speed of 40 yards per minute and at a pressure of about 90 tons.

2. A method of making a reusable surgical/medical fabric as in claim 1, further characterized by the additional step of rinsing the fabric immediately after the dyeing step to assure that the finished product will be free of leveling agents, or the like, which would adversely affect the Suter rating of the finished fabric.

3. A reusable surgical/medical fabric capable of sterile reprocessing, made in accordance with the method of claim 1.

4. A reusable surgical/medical fabric capable of sterile reprocessing,
    said fabric having a woven construction of warp and fill yarns, comprising continuous, multi-filament, polyester yarns,
    the construction of said fabric being further characterized by
        a. warp yarns—false twist 100/100 yarns, fill yarns—air texturized, core and effect, 2/60/100 yarns,
        b. approximately 162 ends per inch, approximately 76 picks per inch,
        c. a weight of approximately 4.1 ounces per square yard,
        d. a thickness of approximately 0.007 inch,
        e. an applied hydrophobic finish, and
        f. said fabric being "lightly" calendered,
    said fabric being further characterized by
        a "hand" which is essentially equivalent to the "hand" of a cotton fabric of similar weight, and by
        a porosity of at least approximately $19.0 \times 10^6$ pores/cm$^2$, and by
        an initial Suter rating of at least 80, and
        said initial Suter rating being reduced no more than 10%–20% after 100 sterile reprocessing cycles.

5. A reusable surgical gown, surgical drape or like surgical/medical item comprising a barrier panel formed of the fabric of claim 4.

6. A reusable surgical gown, surgical drape or like surgical/medical texile product, as in claim 5, further characterized in that
    the barrier panel consists of a single layer of said fabric.

7. A method of making a reusable surgical/medical fabric capable of sterile reprocessing comprising the steps of
    weaving a length of fabric having a greige construction which is plain woven with approximately 153 ends and 75 picks and
    further, in weaving the greige construction, employing continuous filament, multi-filament polyester yarns with
        the warp yarns being a flat, trilobal 100/50, and
        the fill yarns being a 2/60/100 air texturized, core and effect, yarn having a bulked denier of approximately 150,
    scouring the greige fabric in a continuous process to remove sizing and the like,
    feeding the scoured fabric through a dye bath in a continuous process to provide a desired color therefor,
    treating the finished fabric in an aqueous bath comprising a fluorocarbon, hydrophobic agent to impart a hydrophobic surface finish to the fabric,
    drying the fabric and setting the number of ends to approximately 166 and the number of picks to approximately 77, then
    calendering the fabric by a double nip arrangement between steel rolls heated to a temperature of 390° F. at a rate of 20 yards a minute and a pressure of 90 tons.

8. A reusable surgical/medical fabric capable of sterile reprocessing made in accordance with the method of claim 7.

9. A reusable surgical/medical fabric capable of sterile reprocessing,
    said fabric having a woven construction of warp and fill yarns comprising continuous, multi-filament, polyester yarns,
    the construction of said fabric being further characterized in that
        a. the warp yarns are flat, trilobal 100/50 yarns, and the fill yarns are 2/60/100 air texturized, core and effect, yarns having a bulked denier of approximately 150,
        b. approximately 166 ends approximately 77 picks
        c. a weight of approximately 4.0 ounces per square yard,
        d. an applied hydrophobic finish
        e. said fabric is "heavily" calendered,
    said fabric being characterized by
        a "hand" which is essentially equivalent to the "hand" of a cotton fabric of similar weight, and by a porosity of at least approximately 15.1×10⁶ pores per square centimeter, and by an initial Suter rating of 100, and said initial Suter rating being reduced no more than 10%–20% after 100 sterile reprocessing cycles.

10. A reusable surgical gown, surgical drape or like surgical/medical textile product comprising a barrier panel formed of the fabric of claim 9.

11. A reusable surgical gown, surgical drape or like surgical/medical item, as in claim 10, further characterized in that the barrier panel consists of a single layer of said fabric.

12. A method of making a reusable surgical/medical fabric capable of sterile reprocessing, comprising the steps of weaving a length of fabric having a greige construction which is plain woven with approximately 147 ends and 72 picks and further, in weaving the greige construction, employing continuous filament, multi-filament polyester yarns with the warp yarns being double ended false twist 2/50/34 yarns, having a bulked denier of 110 and the fill yarns being false twist 150/200 yarns, scouring the greige fabric, to remove sizing and the like, dyeing the fabric, "mechanically" working the fabric to thereby further distort the yarns and filaments of the fabric and thereby increase its bulk, treating the "mechanically" finished fabric in an aqueous bath comprising a fluorocarbon, hydrophobic agent to impart a hydrophobic finish to the fabric, drying the fabric, setting the number of ends to approximately 160 and the number of picks to approximately 82, then calendering the fabric by a double nip arrangement between steel rolls heated to a temperature of 390° F. at a rate of 20 yards a minute and a pressure of 90 tons.

13. A reusable surgical/medical fabric capable of sterile reprocessing made in accordance with the method of claim 12.

14. A reusable surgical/medical fabric capable of sterile reprocessing, said fabric having a woven construction of warp and fill yarns, comprising continuous, multi-filament, polyester yarns, the construction of said fabric being further characterized in that a. the warp yarns are double ended false twist 2/50/34 yarns, and the fill yarns are false twist 150/200 yarns, b. approximately 160 ends approximately 72 picks c. a weight of approximately 4.2 ounces per square inch, d. an applied hydrophobic finish e. said fabric is "heavily" calendered, said fabric being characterized by a "hand" which is similar to the "hand" of a cotton fabric of similar weight, and by a porosity of approximately 15.1×10⁶ pores per square centimeter, and by an initial Suter rating of at least 80, and said initial Suter rating being reduced no more than 10%–20% after 100 sterile reprocessing cycles.

15. A reusable surgical gown, surgical drape or like surgical/medical item comprising a barrier panel formed of the fabric of claim 14.

16. A reusable surgical gown, surgical drape or like surgical/medical textile product, as in claim 15, further characterized in that the barrier panel consists of a single layer of said fabric.

17. A reusable surgical/medical fabric capable of sterile reprocessing, said fabric being characterized in that it is constructed in substantial part by polyester yarns having a denier to filament ratio no greater than about 1.0, with the remainder of construction substantially comprising polyester yarns having a denier to filament ratio no greater than about 2.5, said filaments defining a multiplicity of pores, said fabric having a Suter rating of at least 50 and a "hand" similar to a "cotton hand", further characterized in that the fabric has a porosity of at least about 10×10⁶ pores/cm².

18. A reusable surgical/medical fabric as in claim 17, further characterized in that the pores have a mean size of no more than about 4.0μ.

19. A reusable surgical/medical fabric as in claim 17, further characterized in that the maximum pore size is no more than about 9.0μ.

20. A reusable surgical/medical fabric as in claim 18, further characterized in that the maximum pore size is no more than about 9.0μ.

21. A reusable surgical/medical fabric as in claim 17, further characterized in that the mean pore size is in the order of 1.5μ to 3.5μ, and the maximum pore size is in the order of 2.0μ to 8.0μ.

22. A reusable surgical/medical fabric as in claim 21, further characterized in that the minimum pore opening is in the order of 0.8μ to 2.5μ.

23. A reusable surgical/medical fabric as in claim 21, further characterized in that the filament density of the fabric is at least about 3.8×10⁶ filaments/in³.

24. A reusable surgical/medical fabric as in claim 17, further characterized in that the filament density of the fabric is at least about 2.0×10⁶ filaments/in³.

25. A reusable surgical/medical fabric as in claim 24, further characterized in that it has a thickness between about 0.003 and 0.008 inches and a weight of at least about 3.5 ounces per square yard and no more than about 5.0 ounces per square yard.

26. A reusable surgical/medical fabric as in claim 24, wherein the fabric is a woven construction of warp and fill yarns and is further characterized in that the fill yarns comprise approximately 40% of the yarn construction, and the warp yarns have a denier less than the denier of the fill yarns, but no more than 40% less than the denier of the fill yarns.

27. A reusable surgical/medical fabric as in claim 26, further characterized in that the fabric has the following, initial barrier properties:

| | |
|---|---|
| Water Resistance: Hydrostatic | 75 (minimum) |

-continued

| | |
|---|---|
| Pressure Test, AATCC[1]-127-80 (Suter) | |
| Water Repellency: Spray Test AATCC 22-1980 | 90 (minimum) |
| Oil Repellency: Hydrocarbon Resistance Test, INDA[2]-80.8 | 3 (minimum) |
| Alcohol Repellency INDA-80.9 | 7 (minimum) |
| Water Resistance: Impact Penetration AATC-42-1975 | 1.0 (maximum) |

[1]American Association of Textile Chemists & Colorists
[2]International Nonwovens & Disposables Test 28. A reusable surgical/medical fabric as in claim 27, further characterized in that
the barrier properties are degraded no more than about 20% after 100 sterile reprocessing cycles.

29. A reusable surgical/medical fabric capable of sterile reprocessing, wherein said fabric
is a woven construction formed by polyester warp and fill yarns, and characterized in that
the warp yarns are multiple ended texturized yarns and have a denier to filament ratio no greater than about 2.0, and
the fill yarns are textured and have a denier to filament ratio no greater than about 1.0.

30. A reusable surgical/medical fabric as in claim 29, further characterized in that
the warp yarns are two ended false twist yarns and have a denier to filament ratio of approximately 1.5, and
the fill yarns are false twist, single ended yarns.

31. A reusable surgical/medical fabric as in claim 30, further characterized in that
the warp yarns are 2/34/50 yarns, and
the fill yarns are 1/150/200 yarns.

32. A reusable surgical/medical fabric as in claim 31, further characterized in that
the fabric is a plain woven construction.

33. A reusable surgical/medical fabric as in claim 31, further characterized in that
the fabric is a 2×1 twill weave construction.

34. A reusable surgical/medical fabric as in claim 29, further characterized in that
the fabric is a plain woven construction.

35. A reusable surgical/medical fabric as in claim 29, further characterized in that
the fabric is a twill weave construction.

36. A reusable surgical/medical fabric as in claim 30, further characterized in that
the fabric has a thickness between about 0.005 inch and 0.009 inch,
the fabric has a filament density of at least about $10 \times 10^6$ filaments/in.$^3$, and the fabric has a porosity of at least $13 \times 10^6$ pores/cm$^2$.

37. A reusable surgical/medical fabric as in claim 36, further characterized in that
its barrier properties are degraded no more than about 20% after 100 sterile reprocessing cycles.

38. A reusable surgical/medical fabric as in claim 36, further characterized in that
it has,
a mean pore size no greater than about 4.0µ, and
a maximum pore size no greater than about 9.0µ.

39. A reusable surgical/medical fabric capable of sterile reprocessing, said fabric being characterized in that
it is a woven construction of polyester yarns and has a "hand" similar to a "cotton hand",
and an initial Suter rating of at least approximately 50, further characterized in that the woven construction is a twill weave.

40. A reusable surgical/medical fabric as in claim 39, further characterized in that
the initial Suter is at least approximately 70 and
the woven construction is a 2×1 twill weave.

41. A reusable surgical/medical fabric as in claim 40, wherein
the woven construction comprises warp and fill yarns and further characterized in that
the warp yarns are multiple ended texturized yarns and have a denier to filament ratio no greater than about 2.0, and
the fill yarns are textured and have a denier to filament ratio no greater than about 1.0.

42. A reusable surgical/medical fabric as in claim 41, further characterized in that
the barrier properties are degraded no more than about 20% after 100 sterile reprocessing cycles.

43. A reusable surgical/medical fabric capable of sterile reprocessing, said fabric being characterized in that
it is a plain woven construction formed of multiple filament, polyester warp and fill yarns wherein
the warp yarns have a relatively large crimp,
the fill yarns have relatively small crimp, and
the filaments of the warp yarns overly at least the majority, of the surfaces of the fill yarns on the top and bottom surfaces of the fabric, whereby the portions of the fabric's surfaces, defined by fill yarns, is minimized further characterized in that
the fill yarns are air texturized core and effect yarns.

44. A reusable surgical/medical fabric as in claim 43, further characterized in that
the filaments of the warp yarns have a trilobal cross section.

45. A reusable surgical/medical fabric as in claim 44, further characterized in that
the warp yarns are flat trilobal 100/50 yarns and
the fill yarns are air texturized core and effect 2/60/100 yarns.

46. A reusable surgical/medical fabric as in claim 43, further characterized in that
the warp yarns are false twist textured yarns.

47. A reusable surgical/medical fabric as in claim 46, further characterized in that
the warp yarns are false twist 100/100 yarns, and
the fill yarns are air texturized core and effect 2/60/100 yarns.

48. A reusable surgical/medical fabric as in claim 47, further characterized in that
the fabric has a thickness between about 0.005 inch and 0.008 inch, and
a weight between about 4.0 ounces and 6.0 ounces per square yard, and
a filament density of at least $10 \times 10^6$ filaments/in$^3$.

49. A reusable surgical/medical fabric capable of sterile reprocessing, said fabric having an initial Suter rating of at least 50 and
wherein the fabric is
a plain woven construction formed of multiple filament, polyester warp and fill yarns wherein, and
further characterized in that
the fill yarns are air texturized core and effect yarns, and
the fabric has a "hand" similar to a "cotton hand".

50. A reusable surgical/medical fabric as in claim 49, further characterized in that
wherein the fill yarns are air texturized core and effect 2/60/100 yarns.

51. A reusable surgical/medical fabric as in claim 49, further characterized in that
the fill yarns comprise approximately 40% of the yarn construction, and
the warp yarns have a denier less than the denier of the fill yarns, but no less than 40% less than the denier of the fill yarns.

52. A reusable surgical/medical fabric as in claim 51, further characterized in that
the warp yarn is a textured yarn.

53. A reusable surgical/medical fabric as in claim 52, further characterized in that
the warp yarns are false twist 100/100 yarns, and
the fill yarns are air texturized core and effect 2/60/100 yarns.

54. A reusable surgical/medical fabric as in claim 53, further characterized in that
it is lightly calendered and has an initial Suter rating of at least about 80, and
it has a pore density of at least about 19.0 pores/cm2,
a mean pore size no greater than about $4.0\mu$, and
a maximum prore size no more than about $9.0\mu$.

55. A reusable surgical/medical fabric as in claim 54, further characterized in that
the barrier properties are degraded no more than about 20% after 100 sterile reprocessing cycles.

56. A reusable surgical/medical fabric capable of sterile reprocessing, wherein the fabric is
a plain woven construction formed of multiple filament, polyester warp and fill yarns, and
further characterized in that
the filaments of the warp yarns have a trilobal cross section,
the fill yarns are textured,
the fabric has
a thickness of at least about 0.004 inch,
a filament density of at least $10 \times 10^6$ filaments/in.$^3$., and
a porosity of at least $12 \times 10^6$ pores/cm.$^2$.

57. A reusable surgical/medical fabric as in claim 56, further characterized in that
the warp yarns are flat trilobal 100/50 yarns.

58. A reusable surgical/medical fabric as in claim 57, further characterized in that
the fill yarns are air texturized core and effect 2/60/100 yarns, and
the fabric has an initial Suter rating of at least about 100, and
the Suter rating degrades in the range of 10% to 20% after 100 sterile reprocessing cycles.

59. A reusable surgical/medical fabric as in claim 58, further characterized in that
it has a pore density of at least $15.0 \times 10^6$ pores/cm$^2$,
a mean pore size no greater than about $3.0\mu$, and
a maximum pore size no greater than about $4.5\mu$.

60. A method of making a reusable surgical/medical fabric capable of sterile reprocessing, said method comprising the steps of
weaving a fabric construction from multiple filament yarns employing textured fill yarns having a denier to filament ratio of no more than approximately 1.0 and warp yarns having a denier to filament ratio of no more than approximately 2.5,
scouring the woven greige fabric construction,
dyeing the woven fabric,
applying a hydrophobic surface finish to the fabric, and
drying the fabric after application of the hydrophobic finish,
characterized by
the step of "mechanically" working the fabric to increase its bulk, prior to the drying step following application of the hydrophobic finish.

61. A method of making a reusable surgical/medical fabric as in claim 60, further characterized in that
the warp yarns employed in weaving the fabric are textured and have a denier to filament ratio no greater than about 1.5.

62. A method of making a reusable surgical/medical fabric as in claim 61, further characterized in that
the "mechanically" working step is performed by processing the fabric in a jet dyeing machine.

63. A method of making a reusable surgical/medical fabric as in claim 62, further characterized in that
the scouring step is a batch process performed by a jet dyeing machine, which also performs the "mechanical" working step.

64. A method of making a reusable surgical/medical fabric as in claim 63, further characterized in that
the scouring step includes processing the fabric in a cleaning liquid, having a temperature of approximately 260° F., for approximately 3 hours.

65. A method of making a reuasble surgical/medical fabric as in claim 63, further characterized in that
the woven fabric is continuously scoured prior to the batch scouring step, and
the batch scouring step includes the use of a detergent liquid have a temperature of approximately 260° F.

66. A method of making a reusable surgical/medical fabric as in claim 60, further characterized by the additional step of
setting the number of ends and picks so that the number of ends is greater in the finished fabric than in the greige fabric, and
the finished fabric has a porosity of at least $10 \times 10^6$ pores/cm$^2$.

67. A method of making a reusable surgical/medical fabric as in claim 60, further characterized in that
the finished fabric has a thickness of between 0.003 inch and 0.008 inch and a weight between 3.0 oz. and 5.0 oz. per square yard, and
the greige construction of the fabric comprises 140–155 ends and 70–86 picks, and
in the setting step,
the number of ends is set between 160 and 170 and the number of picks is set between 70 and 90.

68. A method of making a reusable surgical/medical fabric as in claim 64, further including the additional step of
calendering the fabric subsequent to drying and setting the number of ends and picks.

69. A method of making a reusable surgical/medical fabric as in claim 60, further including
rinsing the fabric after the dyeing step to assure that finished fabric will be free of leveling agents, or the like, which would adversely affect the barrier properties of the finished fabric.

70. A method of making a reusable surgical/medical fabric capable of sterile reprocessing, said method comprising the steps of
weaving a fabric construction from multiple filament yarns employing textured fill yarns having a denier to filament ratio of no more than approximately 1.0 and warp yarns having a denier to filament ratio of no more than approximately 2.5, scouring the woven greige fabric construction, dyeing the woven fabric, applying a hydrophobic surface finish to the fabric, and drying the fabric after application of the hydrophobic finish, characterized by the step of setting the number of ends and picks so that the number of ends is greater in the finished fabric than in the greige fabric, the finished fabric having a porosity of at least $10 \times 10^6$ pores/cm$^2$.

71. A method of making a reusable surgical/medical fabric as in claim 70, further characterized in that the finished fabric has a thickness of between 0.003 inch and 0.008 inch and a weight between 3.0 oz. and 5.0 oz. per square yard.

72. A method of making a reusable surgical/medical fabric as in claim 71, further characterized in that the greige construction of the fabric comprises 140–155 ends and 70–86 picks, and in the setting step, the number of ends is set between 160 and 170 and the number of picks is set between 70 and 90.

73. A method of making a reusable surgical/medical fabric as in claim 70, further characterized in that the step of applying a hydrophobic finish is a continuous process and the setting step is performed in a tenter frame to which the fabric is directly fed to also perform said drying step.

74. A method of making a reusable surgical/medical fabric as in claim 73, including the additional step of calendering the fabric subsequent to drying and setting the number of ends and picks.

75. A method of making a reusable surgical/medical fabric as in claim 70, further characterized in that the calendering step provides a "light" calendering through the use of a heated, smooth, pressure roll and a fiber roll between which the fabric is fed.

* * * * *